US012778493B2

(12) United States Patent
Kumar et al.

(10) Patent No.: US 12,778,493 B2
(45) Date of Patent: Nov. 3, 2026

(54) VISUAL DETERMINATION OF SLEEP STATES

(71) Applicants: The Jackson Laboratory, Bar Harbor, ME (US); The Trustees of the University of Pennsylvania, Philadelphia, PA (US)

(72) Inventors: Vivek Kumar, Bar Harbor, ME (US); Allan I. Pack, Bar Harbor, ME (US); Brian Geuther, Bar Harbor, ME (US); Joshy George, Bar Harbor, ME (US); Mandy Chen, Bar Harbor, ME (US)

(73) Assignees: The Jackson Laboratory, Bar Harbor, ME (US); The Trustees of the University of Pennsylvania, Philadelphia, PA (US)

( * ) Notice: Subject to any disclaimer, the term of this patent is extended or adjusted under 35 U.S.C. 154(b) by 210 days.

(21) Appl. No.: 18/572,717

(22) PCT Filed: Jun. 27, 2022

(86) PCT No.: PCT/US2022/035112

§ 371 (c)(1),
(2) Date: Dec. 20, 2023

(87) PCT Pub. No.: WO2023/278319

PCT Pub. Date: Jan. 5, 2023

(65) Prior Publication Data

US 2024/0293077 A1 Sep. 5, 2024

Related U.S. Application Data

(60) Provisional application No. 63/215,511, filed on Jun. 27, 2021.

(51) Int. Cl.
*A61B 5/00* (2006.01)

(52) U.S. Cl.
CPC .......... *A61B 5/4812* (2013.01); *A61B 5/0077* (2013.01); *A61B 5/4839* (2013.01); *A61B 5/7267* (2013.01); *A61B 2503/40* (2013.01)

(58) Field of Classification Search
CPC ........ G06V 10/26; G06V 10/62; G06V 10/82; G06V 10/85; G06V 20/52; G06V 20/70;
(Continued)

(56) References Cited

U.S. PATENT DOCUMENTS

| | | | | |
|---|---|---|---|---|
| 2019/0001241 | A1 | 1/2019 | Miller et al. | |
| 2019/0091241 | A1 * | 3/2019 | Barbut | A61K 31/5513 |
| 2021/0169417 | A1 | 6/2021 | Burton | |

FOREIGN PATENT DOCUMENTS

| | | |
|---|---|---|
| EP | 2 246 799 | 11/2010 |
| EP | 3 628 213 | 4/2020 |

(Continued)

OTHER PUBLICATIONS

Int'l Search Report mailed on Nov. 3, 2022, in connection with International Application No. PCT/US2022/035112, filed on Jun. 27, 2022, 2 pages.

(Continued)

*Primary Examiner* — Amanda K Hulbert
(74) *Attorney, Agent, or Firm* — McDonnell Boehnen Hulbert & Berghoff LLP

(57) ABSTRACT

Systems and methods described herein provide techniques for determining sleep state data by processing video data of a subject. Systems and methods may determine a plurality of features from the video data, and may determine sleep state data for the subject using the plurality of features. In some embodiments, the sleep state data may be based on frequency domain features and/or time domain features corresponding to the plurality of features.

18 Claims, 21 Drawing Sheets

(58) Field of Classification Search
CPC .... G06V 40/10; G06V 40/20; A61B 2503/40; A61B 5/0077; A61B 5/4812; A61B 5/4839; A61B 5/7267
See application file for complete search history.

(56) References Cited

FOREIGN PATENT DOCUMENTS

| | | | |
|---|---|---|---|
| WO | 2020/064580 | A1 | 4/2020 |
| WO | 2020176759 | A1 | 9/2020 |

OTHER PUBLICATIONS

Written Opinion mailed on Nov. 3, 2022, in connection with International Application No. PCT/US2022/035112, filed on Jun. 27, 2022, 7 pages.
Extended European Search Report from European Application No. 22833991.7, dated Mar. 27, 2025.
T. Nochino et al., "Sleep stage estimation method using a camera for home use," Biomedical Engineering Letters (2019) 9:257-265.
B. B. McShane, et al., "Assessing REM Sleep in Mice Using Video Data," Sleep, vol. 35, No. 3, Mar. 2012, 433-442F.
Examination Report from Indian Application No. 202417002856, dated Apr. 7, 2026.

* cited by examiner

| | Precision | Recall | F1-Score |
|---|---|---|---|
| Wake | 0.984 | 0.961 | 0.972 |
| NREM | 0.951 | 0.914 | 0.932 |
| REM | 0.535 | 0.897 | 0.664 |

VISUAL DETERMINATION OF SLEEP STATES

RELATED APPLICATIONS

This application is the U.S. national phase under 35 U.S.C. § 371 of International Application No. PCT/US2022/035112, filed Jun. 27, 2022, which claims benefit under 35 U.S.C § 119(e) of U.S. Provisional Application Ser. No. 63/215,511 filed Jun. 27, 2021, the disclosures of which are incorporated by reference herein in its-their entirety.

GOVERNMENT SUPPORT

This invention was made with government support under DA041668 (NIDA), DA048634 (NIDA), and HL094307 (NHLBI) granted by National Institutes of Health. The government has certain rights in the invention.

FIELD OF THE INVENTION

The invention, in some aspects, relates to determining a sleep state of a subject by processing video data using machine learning models.

BACKGROUND

Sleep is a complex behavior that is regulated by a homeostatic process and whose function is critical for survival. Sleep and circadian disturbances are seen in many diseases including neuropsychiatric, neurodevelopmental, neurodegenerative, physiologic, and metabolic disorders. Sleep and circadian functions have a bidirectional relationship with these diseases, in which changes in sleep and circadian patterns can lead to or be the cause of the disease state. Even though the bidirectional relationships between sleep and many diseases have been well described, their genetic etiologies have not been fully elucidated. In fact, treatments for sleep disorders are limited because of a lack of knowledge about sleep mechanisms. Rodents serve as a readily available model of human sleep due to similarities in sleep biology, and mice, in particular, are a genetically tractable model for mechanistic studies of sleep and potential therapeutics. One of the reasons for this critical gap in treatment is due to technological barriers that prevent reliable phenotyping of large numbers of mice for assessment of sleep states. The gold standard of sleep analysis in rodents utilizes electroencephalogram/electromyogram (EEG/EMG) recordings. This method is low throughput as it requires surgery for electrode implantation and often requires manual scoring of the recordings. Although new methods utilizing machine learning models have started to automate EEG/EMG scoring, the data generation is still low-throughput. In addition, the use of tethered electrodes limits animal movement potentially altering animal behavior.

Some existing systems have explored some non-invasive approaches for sleep analysis to overcome low-throughput limitation. These include activity assessment through beam break systems, or videography in which certain amount of inactivity is interpreted as sleep. Piezo pressure sensors have also been used as a simpler and more sensitive method of accessing activity. However, these methods only assess sleep versus wake status, and are not able to differentiate between wake state, rapid eye movement (REM) state, and non-REM state. This is critical because activity determination of sleep states can be inaccurate in humans as well as rodents that have low general activity. Other methods to assess sleep states include pulse Doppler-based method to access movement and respiration, and whole body plethysmography to directly measure breathing patterns. Both these approaches require specialized equipment. Electric field sensors that detect respiration and other movements have also been used to assess sleep states.

SUMMARY OF THE INVENTION

According to an embodiment of the invention, a computer-implemented method is provided, the method including: receiving video data representing a video of a subject; determining, using the video data, a plurality of features corresponding to the subject; and determining, using the plurality of features, sleep state data for the subject. In some embodiments, the method also includes: processing, using a machine learning model, the video data to determine segmentation data indicating first set of pixels corresponding to the subject and second set of pixels corresponding to the background. In some embodiments, the method also includes processing the segmentation data to determine ellipse fit data corresponding to the subject. In some embodiments, determining the plurality of features includes processing the segmentation data to determine the plurality of features. In some embodiments, the plurality of features includes a plurality of visual features for each video frame of the video data. In some embodiments, the method also includes determining time domain features for each visual feature of the plurality of visual features, and wherein the plurality of features includes the time domain features. In some embodiments, determining the time domain features includes determining one of: kurtosis data, mean data, median data, standard deviation data, maximum data, and minimum data. In some embodiments, the method also includes determining frequency domain features for each visual feature of the plurality of visual features, and wherein the plurality of features includes the frequency domain features. In some embodiments, determining the frequency domain features includes determining one of: kurtosis of power spectral density, skewness of power spectral density, mean power spectral density, total power spectral density, maximum data, minimum data, average data, and standard deviation of power spectral density. In some embodiments, the method also includes determining time domain features for each of the plurality of features; determining frequency domain features for each of the plurality of features; processing, using a machine learning classifier, the time domain features and the frequency domain features to determine the sleep state data. In some embodiments, the method also includes processing, using a machine learning classifier, the plurality of features to determine a sleep state for a video frame of the video data, the sleep state being one of a wake state, a REM sleep state and a non-REM (NREM) sleep state. In some embodiments, the sleep state data indicates one or more of a duration of time of a sleep state, a duration and/or frequency interval of one or more of a wake state, a REM state, and a NREM state; and a change in one or more sleep states. In some embodiments, the method also includes determining, using the plurality of features, a plurality of body areas of the subject, each body area of the plurality of body areas corresponding to a video frame of the video data; and determining the sleep state data based on changes in the plurality of body areas during the video. In some embodiments, the method also includes determining, using the plurality of features, a plurality of width-length ratios, each width-length ratio of the plurality of width-length ratios corresponding to a video frame of the video data; and determining the sleep state data based on changes in the plurality of width-length ratios during the video. In some embodiments, determining the sleep state data includes: detecting a transition from a NREM state to a REM state based on a change in a body area or body shape of the subject, the change in the body area or body shape being a result of muscle atonia. In some embodiments, the method also includes: determining a plurality of width-length ratios for the subject, a width-length ratio of the plurality of width-length ratios corresponding to a video frame of the video data; determining time domain features using the plurality of width-length ratios; determining frequency domain features using the plurality of width-length ratios, wherein the time domain features and the frequency domain features represent motion of an abdomen of the subject; and determining the sleep state data using the time domain features and the frequency domain features. In some embodiments, the video captures the subject in the subject's natural state. In some embodiments, the subject's natural state includes the absence of an invasive detection means in or on the subject. In some embodiments, the invasive detection means includes one or both of an electrode attached to and an electrode inserted into the subject. In some embodiments, the video is a high-resolution video. In some embodiments, the method also includes:

processing, using a machine learning classifier, the plurality of features to determine a plurality of sleep state predictions each for one video frame of the video data; and processing, using a transition model, the plurality of sleep state predictions to determine a transition between a first sleep state to a second sleep state. In some embodiments, the transition model is a Hidden Markov Model. In some embodiments, the subject is a rodent, and optionally is a mouse. In some embodiments, the subject is a genetically engineered subject.

According to another aspect of the invention, a method of determining a sleep state in a subject is provided, the method including monitoring a response of the subject, wherein a means of the monitoring includes any embodiment of an aforementioned computer-implemented method. In some embodiments, the sleep state includes one or more of a stage of sleep, a time period of a sleep interval, a change in a sleep stage, and a time period of a non-sleep interval. In some embodiments, the subject has a sleep disorder or condition. In some embodiments, the sleep disorder or condition includes one or more of: sleep apnea, insomnia, and narcolepsy. In some embodiments, the sleep disorder or condition is a result of a brain injury, depression, psychiatric illness, neurodegenerative illness, restless leg syndrome, Alzheimer's disease, Parkinson's disease, obesity, overweight, effects of an administered drug, and/or effects of ingesting alcohol a neurological condition capable of altering a sleep state status, or a metabolic disorder or condition capable of altering a sleep state. In some embodiments, the method also includes administering to the subject is a therapeutic agent prior to the receiving of the video data. In some embodiments, the therapeutic agent includes one or more of a sleep enhancing agent, a sleep inhibiting agent, and an agent capable of altering one or more sleep stages in the subject. In some embodiments, the method also includes administering a behavioral treatment to the subject. In some embodiments, the behavioral treatment includes a sensory therapy. In some embodiments, the sensory therapy is a light-exposure therapy. In some embodiments, the subject is a genetically engineered subject. In some embodiments, the subject is a rodent, and optionally is a mouse. In some embodiments, the mouse is a genetically engineered mouse. In some embodiments, the subject is an animal model of a sleep condition. In some embodiments, the determined sleep state data for the subject is compared to a control sleep state data. In some embodiments, the control sleep state data is sleep state data from a control subject determined with the computer-implemented method. In some embodiments, the control subject does not have the sleep disorder or condition of the subject. In some embodiments, the control subject is not administered the therapeutic agent or behavioral treatment administered to the subject. In some embodiments, the control subject is administered a dose of the therapeutic agent that is different than the dose of the therapeutic agent administered to the subject.

According to another aspect of the invention, a method of identifying efficacy of a candidate therapeutic agent and/or candidate behavioral treatment to treat a sleep disorder or condition in a subject is provided, the method including: administering to a test subject the candidate therapeutic agent and/or candidate behavioral treatment and determining sleep state data for the test subject, wherein a means of the determining includes any embodiment of any aforementioned computer-implemented method, and wherein a determination indicating a change in the sleep state data in the test subject identifies an effect of the candidate therapeutic agent or the candidate behavioral treatment, respectively, on the sleep disorder or condition in the subject. In some embodiments, the sleep state data includes data of one or more of a stage of sleep, a time period of a sleep interval, a change in a sleep stage, and a time period of a non-sleep interval. In some embodiments, the test subject has a sleep disorder or condition. In some embodiments, the sleep disorder or condition includes one of more of: sleep apnea, insomnia, and narcolepsy. In some embodiments, the sleep disorder or condition is a result of a brain injury, depression, psychiatric illness, neurodegenerative illness, restless leg syndrome, Alzheimer's disease, Parkinson's disease, obesity, overweight, effects of an administered drug, and/or effects of ingesting alcohol a neurological condition capable of altering a sleep state status, or a metabolic disorder or condition capable of altering a sleep state. In some embodiments, the candidate therapeutic agent and/or candidate behavioral treatment is administered to the test subject at one or more of prior to or during the receiving of the video data. In some embodiments, the candidate therapeutic agent comprises one or more of a sleep enhancing agent, a sleep inhibiting agent, and an agent capable of altering one or more sleep stages in the test subject. In some embodiments, the behavioral treatment includes a sensory therapy. In some embodiments, the sensory therapy is a light-exposure therapy. In some embodiments, the subject is a genetically engineered subject. In some embodiments, the test subject is a rodent, and optionally is a mouse. In some embodiments, the mouse is a genetically engineered mouse. In some embodiments, the test subject is an animal model of a sleep condition. In some embodiments, the determined sleep state data for the test subject is compared to a control sleep state data. In some embodiments, the control sleep state data is sleep state data from a control subject determined with the computer-implemented method. In some embodiments, the control subject does not have the sleep disorder or condition of the test subject. In some embodiments, the control subject is not administered the candidate therapeutic agent administered to the test subject. In some embodiments, the control subject is administered a dose of the candidate therapeutic agent that is different than the dose of the candidate therapeutic agent administered to the test subject. In some embodiments, the control subject is administered a regimen of the candidate behavioral therapy that is different than the regimen of the candidate therapeutic agent administered to the test subject. In some embodiments, the regimen of the behavioral treatment includes characteristics of the treatment such as one or more of: a length of the behavioral treatment, an intensity of the behavioral treatment, a light intensity in the behavioral treatment, and a frequency of the behavioral treatment.

BRIEF DESCRIPTION OF THE DRAWINGS

For a more complete understanding of the present disclosure, reference is now made to the following description taken in conjunction with the accompanying drawings.

FIG. 8A shows exemplar spectral analysis plots for REM and NREM epochs. The continuous wavelet transform spectral response (top panels) and associated dominant signal (respective lower left panels), and a histogram of the dominant signal (respective lower right panels). NREM epochs typically showed a lower mean and standard deviation than REM epochs. FIG. 8B shows a plot inspecting a larger time scale of epochs indicating that the NREM signal was stable until a bout of REM. Dominant frequencies were typical mouse breathing rate frequencies.

FIG. 9A shows the mobility cutoff used to select for sleeping epochs in C57BL/6J vs C3H/HeJ breathing rate analysis. Below the 10% quantile cutoff threshold (black vertical line), epochs consisted of 90.2% NREM (red line), 8.1% REM (green line), and 1.7% wake (blue line). FIG. 9B shows comparisons between strains of dominant frequency observed in sleeping epochs (blue, male; orange, female). FIG. 9C shows that using the C57BL/6J annotated epochs, a higher standard deviation was observed in dominant frequency in REM state (blue line) than in NREM state (orange line).

FIG. 10A shows classifier performance compared at different stages, starting with the XgBoost classifier, adding an HMM model, increasing features to include seven Hu moments, and integrating SPINDLE annotations to improve epoch quality. It was observed that the overall accuracy improved by adding each of these steps. FIG. 10B shows the top 20 most important features for the classifier. FIG. 10C shows a confusion matrix obtained from 10-fold cross validation. FIG. 10D shows a precision-recall table.

FIG. 11A shows a hypnogram of visual scoring and EEG/EMG scoring. FIG. 11B shows a plot of a 24-hour visual scored sleep stage (top) and predicted stage (bottom) for a mouse (B6J_7). FIG. 11C-D shows a comparison of human and visual scoring across all C57BL/6J mice demonstrating high concordance between the two methods. Data were plotted in 1 hour bins across 24 hours (FIG. 11C) and in 24 or 12 hour periods (FIG. 11D).

DETAILED DESCRIPTION

The present disclosure relates to determining sleep states of a subject by processing video data for the subject using one or more machine learning models. Respiration, movement, or posture, of a subject, by themselves are useful for distinguishing between the sleep states. In some embodiments of the present disclosure, a combination of respiration, movement and posture features are used to determine the sleep states of the subject. Using a combination of these features increases the accuracy of predicting the sleep states. The term "sleep state" is used in reference to rapid eye movement (REM) sleep state and non-rapid eye movement (NREM) sleep state. Methods and systems of the invention can be used to assess and distinguish between a REM sleep state, a NREM sleep state, and a wake (non-sleep) state in a subject.

To identify wake states, NREM states and REM states, in some embodiments, a video-based method with high resolution video is used based on determining that information about sleep states is encoded in video data. There are subtle changes observed in the area and shape of a subject as it transitions from NREM state to REM state, likely due to the atonia of the REM state. Over the past few years, large improvements have been made in the field of computer vision, largely due to advancement in machine learning, particularly in the field of deep learning. Some embodiments use advanced machine vision methods to greatly improve upon visual sleep state classification. Some embodiments involve extracting features from the video data that relate to respiration, movement, and/or posture of the subject. Some embodiments combine these features to determine sleep states in subjects, such as, mice for example. Embodiments of the present disclosure involve non-invasive video-based methods that can be implemented with low hardware investment and that yield high quality sleep state data. The ability to access sleep states reliably, non-invasively, and in a high throughput manner will enable large scale mechanistic studies necessary for therapeutic discoveries.

Figure 1:
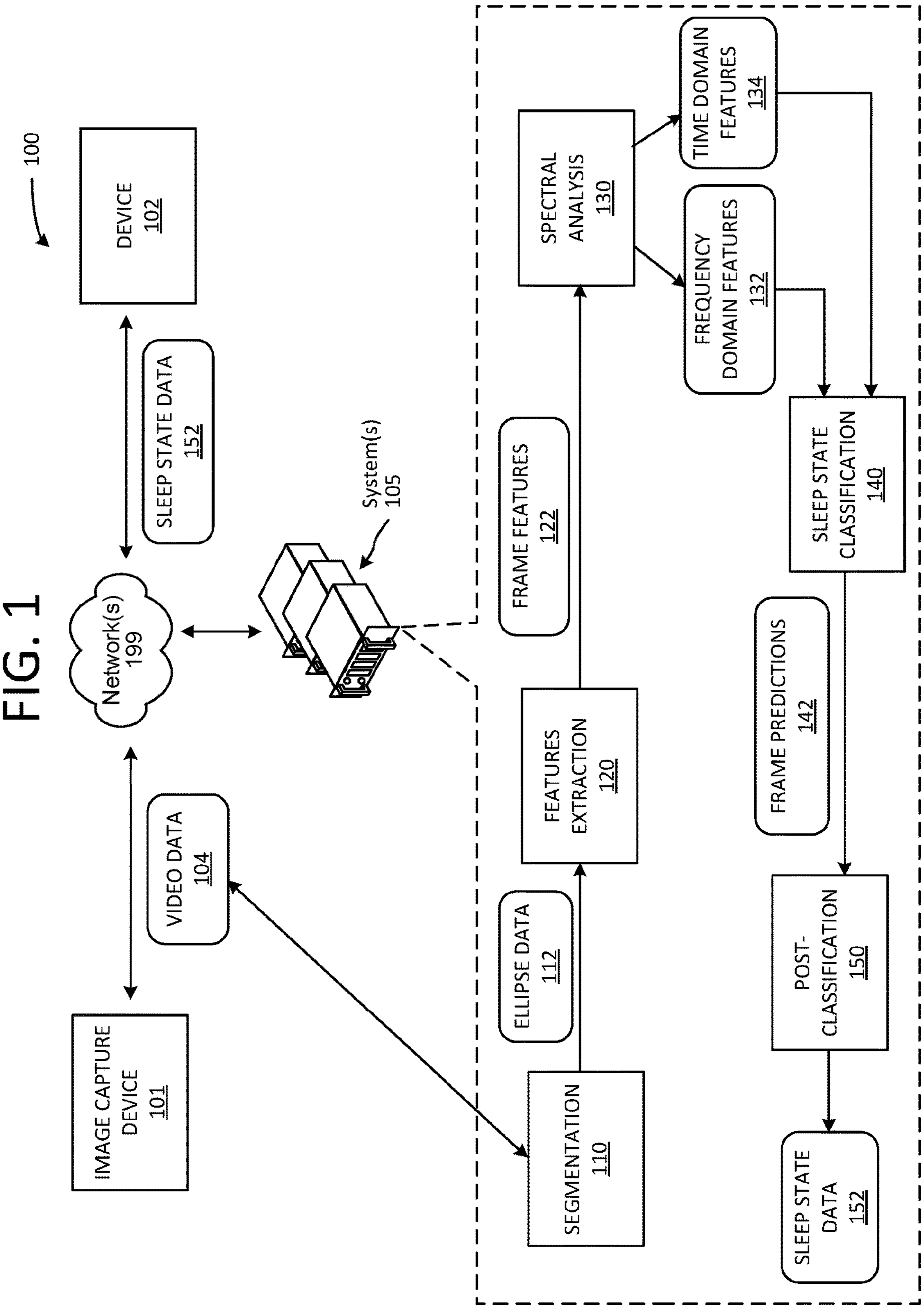
FIG. 1 is a conceptual diagram of a system for determining sleep state data for a subject using video data, according to embodiments of the present disclosure.

FIG. 1 conceptually illustrates a system 100 (e.g., an automated sleep state system 100) for determining sleep state data for a subject using video data. The automated sleep state system 100 may operate using various components as illustrated in FIG. 1. The automated sleep state system 100 may include an image capture device 101, a device 102 and one or more systems 105 connected across one or more networks 199. The image capture device 101 may be part of, included in, or connected to another device (e.g., device 400 shown in FIG. 4), and may be a camera, a high speed video camera, or other types of devices capable of capturing images and videos. The device 101, in addition to or instead of an image capture device, may include a motion detection sensor, infrared sensor, temperature sensor, atmospheric conditions detection sensor, and other sensors configured to detect various characteristics/environmental conditions. The device 102 may be a laptop, a desktop, a tablet, a smartphone, or other types of computing devices capable of displaying data, and may include one or more components described in connection with device 400 below.

The image capture device 101 may capture video (or one or more images) of a subject, and may send video data 104 representing the video to the system(s) 105 for processing as described herein. The video may be of the subject in an open field arena. In some cases, the video data 104 may correspond to images (image data) captured by the device 101 at certain time intervals, such that the images captures the subject over a period of time. In some embodiments, the video data 104 may be a high-resolution video of the subject.

The system(s) 105 may include one or more components shown in FIG. 1, and may be configured to process the video data 104 to determine sleep state data for the subject. The system(s) 105 may generate sleep state data 152 corresponding to the subject, where the sleep state data 152 may indicate one or more sleep states (e.g., a wake/non-sleep state, a NREM state, and a REM state) of the subject observed during the video. The system(s) 105 may send the sleep state data 152 to the device 102 for output to a user to observe the results of processing the video data 104.

In some embodiments, the video data 104 may include video of more than one subject, and the system(s) 105 may process the video data 104 to determine sleep state data for each subject represented in the video data 104.

The system(s) 105 may be configured to determine various data from the video data 104 for the subject. For determining the data and for determining the sleep state data 152, the system(s) 105 may include multiple different components. As shown in FIG. 1, the system(s) 105 may include a segmentation component 110, a features extraction component 120, a spectral analysis component 130, a sleep state classification component 140, and a post-classification component 150. The system(s) 105 may include fewer or more components than shown in FIG. 1. These various components, in some embodiments, may be located on the same physical system 105. In other embodiments, one or more of the various components may be located on different/separate physical systems 105. Communication between the various components may occur directly or may occur across a network(s) 199. Communication between the device 101, the system(s) 105 and the device 102 may occur directly or across a network(s) 199.

In some embodiments, one or more components shown as part of the system(s) 105 may be located at the device 102 or at a computing device (e.g., device 400) connected to the image capture device 101.

At a high level, the system(s) 105 may be configured to process the video data 104 to determine multiple features corresponding to the subject, and determine the sleep state data 152 for the subject using the multiple features.

Figure 2A:
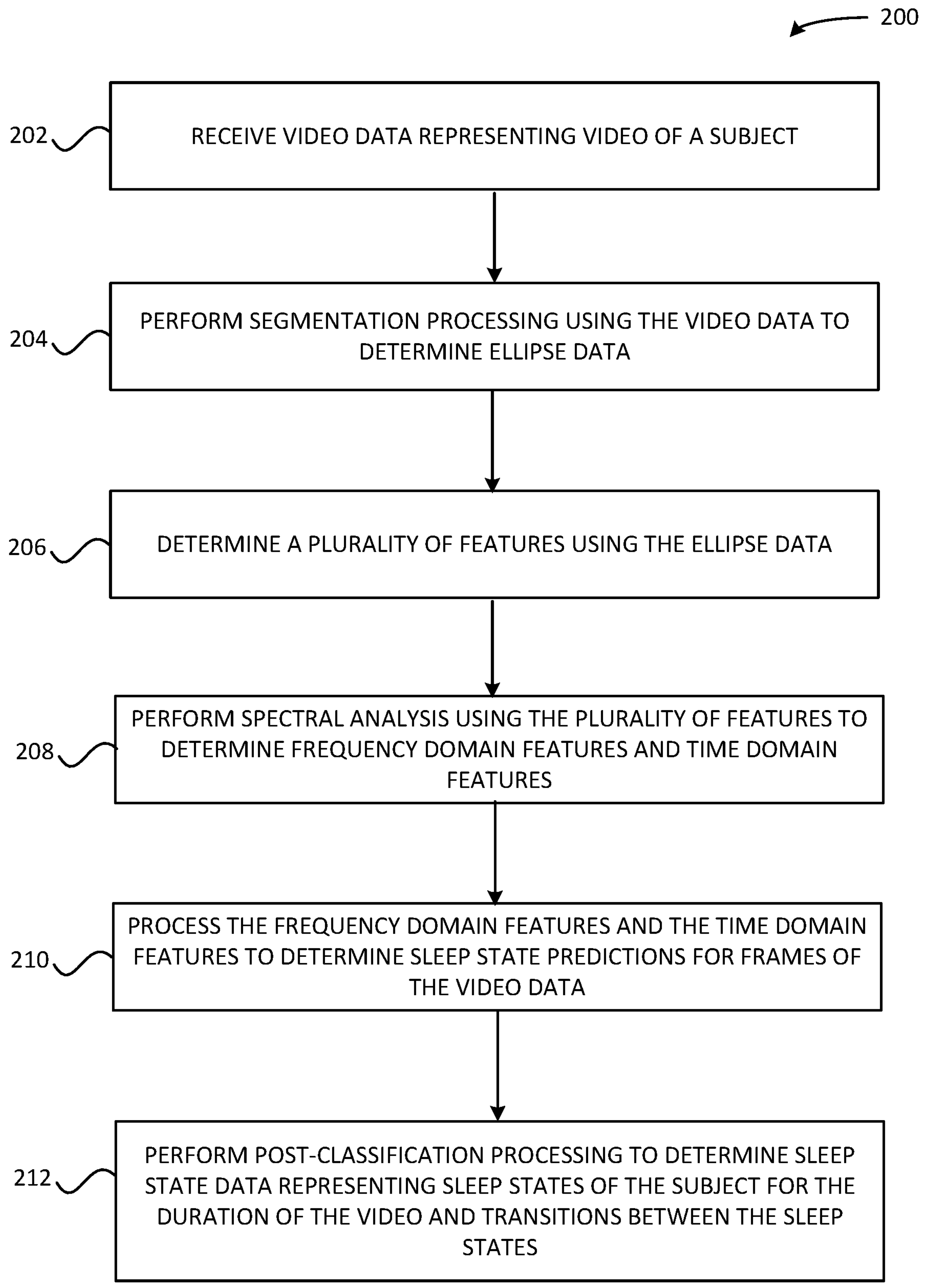
FIG. 2A is a flowchart illustrating a process for determining the sleep state data, according to embodiments of the present disclosure.

FIG. 2A is a flowchart illustrating a process 200 for determining sleep state data 152 for the subject, according to embodiments of the present disclosure. One or more of the steps of the process 200 may be performed in another order/sequence than shown in FIG. 2A. One or more steps of the process 200 may be performed by the components of the system(s) 105 illustrated in FIG. 1.

At a step 202 of the process 200 shown in FIG. 2A, the system(s) 105 may receive the video data 104 representing video of a subject. In some embodiments, the video data 104 may be received by the segmentation component 110 or may be provided to the segmentation component 110 by the system(s) 105 for processing. In some embodiments, the video data 104 may be video capturing the subject in its natural state. The subject may be in its natural state when there are no invasive methods applied to the subject (e.g., no electrodes inserted in or attached to the subject, no dye/color markings applied to the subject, no surgical methods performed on the subject, no invasive detection means in or on the subject, etc.). The video data 104 may be a high-resolution video of the subject.

At a step 204 of the process 200 shown in FIG. 2A, the segmentation component 110 may perform segmentation processing using the video data 104 to determine ellipse data 112 (shown in FIG. 1). The segmentation component 110 may employ techniques to process the video data 104 to generate a segmentation mask identifying the subject in the video data 104, and then generate an ellipse fit/representation for the subject. The segmentation component 110 may employ one or more techniques (e.g., one or more ML models) for object tracking in video/image data, and may be configured to identify the subject. The segmentation component 110 may generate a segmentation mask for each video frame of the video data 104. The segmentation mask may indicate which pixels in the video frame correspond to the subject and/or which pixels in the video frame correspond to a background/non-subject. The segmentation component 110 may process, using a machine learning model, the video data 104 to determine segmentation data indicating first set of pixels corresponding to the subject and second set of pixels corresponding to the background.

A video frame, as used herein, may be a portion of the video data 104. The video data 104 may be divided into multiple portions/frames of the same length/time. For example, a video frame may be 1 millisecond of the video data 104. In determining data, like the segmentation mask, for a video frame of the video data 104, the components of the system(s) 105, like the segmentation component 110, may process a set of video frames (a window of video frames). For example, to determine a segmentation mask for an instant video frame, the segmentation component 110 may process (i) a set of video frames occurring (with respect to time) prior to the instant video frame (e.g., 3 video frames prior to the instant video frame), (ii) the instant video frame, and (iii) a set of video frames occurring (with respect to time) after the instant video frame (e.g., 3 video frames after the instant video frames). As such, in this example, the segmentation component 110 may process 7 video frames for determining a segmentation mask for one video frame. Such processing may be referred to herein as window-based processing of video frames.

Using the segmentation masks for the video data 104, the segmentation component 110 may determine the ellipse data 112. The ellipse data 112 may be an ellipse fit for the subject (an ellipse drawn around the subject's body). For a different type of subject, the system(s) 105 may be configured to determine a different shape fit/representation (e.g., a circle fit, a rectangle fit, a square fit, etc.). The segmentation component 110 may determine the ellipse data 112 as a subset of the pixels in the segmentation mask that correspond to the subject. The ellipse data 112 may include this subset of pixels. The segmentation component 110 may determine an ellipse fit of the subject for each video frame of the video data 104. The segmentation component 110 may be determine the ellipse fit for a video frame using the window-based processing of video frames described above. The ellipse data 112 may be a vector or a matrix of the pixels representing the ellipse fit for all the video frames of the video data 104. The segmentation component 110 may process the segmentation data to determine ellipse fit data 112 corresponding to the subject.

In some embodiments, the ellipse data 112 for the subject may define some parameters of the subject. For example, the ellipse fit may correspond to the subject's location, and may include coordinates (e.g., x and y) representing a pixel location (e.g., the center of the ellipse) of the subject in a video frame(s) of the video data 104. The ellipse fit may correspond to a major axis length and a minor axis length of the subject. The ellipse fit may include a sine and cosine of a vector angle of the major axis. The angle may be defined with respect to the direction of the major axis. The major axis may extend from a tip of the subject's head or nose to an end of the subject's body such as a tail base. The ellipse fit may also correspond to a ratio between the major axis length and the minor axis length of the subject. In some embodiments, the ellipse data 112 may include the foregoing measurements for all video frames of the video data 104.

In some embodiments, the segmentation component 110 may use one or more neural networks for processing the video data 104 to determine the segmentation mask and/or the ellipse data 112. In other embodiments, the segmentation component 110 may use other ML models, such as, an encoder-decoder architecture to determine the segmentation mask and/or the ellipse data 112.

The ellipse data 112 may also include a confidence score(s) of the segmentation component 110 in determining the ellipse fit for the video frame. The ellipse data 112 may alternatively include a probability or likelihood of the ellipse fit corresponding to the subject.

In the embodiments where the video data 104 captures more than one subject, the segmentation component 110 may identify each of the captured subject, and may determine the ellipse data 112 for each of the captured subject. The ellipse data 112 for each of the subject may be provided separately to the features extraction component 120 for processing (in parallel or sequential).

At a step 206 of the process 200 shown in FIG. 2A, the features extraction component 120 may determine a plurality of features using the ellipse data 112. The features extraction component 120 may determine the plurality of features for each video frame in the video data 104. In some example embodiments, the features extraction component 120 may determine 16 features for each video frame of the video data 104. The determined features may be stored as frame features data 122 shown in FIG. 1. The frame features data 122 may be a vector or matrix including values for the plurality features corresponding to each video frame of the video data 104. The features extraction component 120 may determine the plurality of features by processing the segmentation data (determined by the segmentation component 110) and/or the ellipse data 112.

The features extraction 120 may determine the plurality of features to include a plurality of visual features of the subject for each video frame of the video data 104. Below are example features determined by the features extraction component 120 and that may be included in the frame features data 122.

The features extraction component 120 may process the pixel information included in the ellipse data 112. In some embodiments, the features extraction component 120 may determine a major axis length, a minor axis length, and a ratio of the major and minor axis lengths for each video frame of the video data 104. These features may already be included in the ellipse data 112, or the features extraction component 120 may determine these features using the pixel information included in the ellipse data 112. The features extraction component 120 may also determine an area (e.g., a surface area) of the subject using the ellipse fit information included in the ellipse data 112. The features extraction component 120 may determine a location of the subject represented as a center pixel of the ellipse fit. The features extraction component 120 may also determine a change in the location of the subject based on a change in the center pixel of the ellipse fit from one video frame to another (subsequently occurring) video frame of the video data 104. The features extraction component 120 may also determine a perimeter (e.g., a circumference) of the ellipse fit.

The features extraction component 120 may determine one or more (e.g., 7) Hu Moments. Hu Moments (also known as Hu moment invariants) may be a set of seven numbers calculated using central moments of an image/video frame that are invariant to image transformations. The first six moments have been proved to be invariant to translation, scale, rotation, and reflection, while the seventh moment's sign changes for image reflection. In image processing, computer vision and related fields, an image moment is a certain particular weighted average (moment) of the image pixels' intensities, or a function of such moments, usually chosen to have some attractive property or interpretation. Image moments are useful to describe the subject after segmentation. The features extraction component 120 may determine Hu image moments that are numerical descriptions of the segmentation mask of the subject through integration and linear combinations of central image moments.

At a step 208 of the process 200 shown in FIG. 2A, the spectral analysis component 130 may perform spectral analysis using the plurality of features to determine frequency domain features 132 and time domain features 134. In spectral analysis component 130 may use signal processing techniques to determine the frequency domain features 132 and the time domain features 134 from the frame features data 122. In some embodiments, the spectral analysis component 130 may determine, for each feature (from the feature data 122) for each video frame of the video data 104 in an epoch, a set of time domain features and a set of frequency domain features. In example embodiments, the spectral analysis component 130 may determine six time domain features for each feature for each video frame in an epoch. In some embodiments, the spectral analysis component 130 may determine fourteen frequency domain features for each feature for each video frame in an epoch. An epoch may be a duration of the video data 104, for example, 10 seconds, 5 seconds, etc. The frequency domain features 132 may be a vector or matrix representing the frequency domain features determined for each feature in the feature data 122 and for each epoch of video frames. The time domain features 134 may be a vector or matrix representing the time domain features determined for each feature in the feature data 122 and for each epoch of video frames. The frequency domain features 132 may be graph data, for example, as illustrated in FIGS. 7A-7B, 8A-8B.

In example embodiments, the frequency domain features 132 may be kurtosis of power spectral density, skewness of power spectral density, mean power spectral density for 0.1 to 1 Hz, mean power spectral density for 1 to 3 Hz, mean power spectral density for 3 to 5 Hz, mean power spectral density for 5 to 8 Hz, mean power spectral density for 8 to 15 Hz, total power spectral density, maximum value of the power spectral density, minimum value of the power spectral density, average of the power spectral density, and a standard deviation of the power spectral density.

In example embodiments, the time domain features 134 may be kurtosis, mean of the feature signal, median of the feature signal, standard deviation of the feature signal, maximum value of the feature signal, and minimum value of the feature signal.

At a step 210 of the process 200 shown in FIG. 2A, the sleep state classification component 140 may process the frequency domain features 132 and the time domain features 134 to determine sleep predictions for video frames of the video data 104. The sleep state classification component 140 may determine a label, for each video frame of the video data 104, representing a sleep state. The sleep state classification component 140 may classify each video frame into one of three sleep states: a wake state, a NREM state, and a REM state. The wake state may be a non-sleep state or may be similar to a non-sleep state. The sleep state classification component 140 may determine the sleep state label for the video frame using the frequency domain features 132 and the time domain features 134. The sleep state classification component 140, in some embodiments, may use a window-based processing for the video frames described above. For example, to determine the sleep state label for an instant video frame, the sleep state classification component 140 may process data (the time and frequency domain features 132, 134) for a set of video frames occurring prior to the instant video frame and the data for a set of video frames occurring after the instant video frame. The sleep state classification component 140 may output frame predictions data 142, which may be a vector or a matrix of sleep state labels for each video frame of the video data 104. The sleep state classification component 140 may also determine a confidence score associated with the sleep state label, where the confidence score may represent a likelihood of the video frame corresponding to the indicated sleep state, or a confidence of the sleep state classification component 140 in determining the sleep state label of the video frame. The confidence scores may be included in the frame predictions data 142.

The sleep state classification component 140 may employ one or more ML models to determine the frame predictions data 142 from the frequency domain features 132 and the time domain features 134. In some embodiments, the sleep state classification component 140 may use a gradient boosting ML technique (e.g., XGBoost technique). In other embodiments, the sleep state classification component 140 may use a random forest ML technique. In yet other embodiments, the sleep state classification component 140 may use a neural network ML technique (e.g., a multilayer perceptron (MLP)). In yet other embodiments, the sleep state classification component 140 may use a logistic regression technique. In yet other embodiments, the sleep state classification component 140 may use a singular value decomposition (SVD) technique. In some embodiments, the sleep state classification component 140 may use a combination of one or more of the foregoing ML techniques. The ML techniques may be trained to classify video frames of video data for a subject into sleep states, as described in relation to FIG. 3 below.

In some embodiments, the sleep state classification component 140 may use additional or alternative data/features (e.g., the video data 104, the ellipse data 112, frame features data 122, etc.) to determine the frame predictions data 142.

The sleep state classification component 140 may be configured to recognize a transition between one sleep state to another sleep state based on variations between the frequency and time domain features 132, 134. For example, the frequency domain signal and the time domain signal for the area of the subject varies in time and frequency for the wake state, the NREM state and the REM state. As another example, the frequency domain signal and the time domain signal for the width-length ratio (ratio of the major axis length and the minor axis length) of the subject varies in time and frequency for the wake state, the NREM state and the REM state. In some embodiments, the sleep state classification component 140 may use one of the plurality of features (e.g., subject body area or width-length ratio) to determine the frame predictions data 142. In other embodiments, the sleep state classification component 140 may use a combination of features from the plurality of features (e.g., subject body area and width-length ratios) to determine the frame predictions data 142.

At a step 212 of the process 200 shown in FIG. 2A, the post-classification component 150 may perform post-classification processing to determine the sleep state data 152 representing sleep states of the subject for the duration of the video and transitions between the sleep states. The post-classification component 150 may process the frame predictions data 142, including a sleep state label for each video frame (and a corresponding confidence score), to determine the sleep state data 152. The post-classification component 150 may use a transition model to determine a transition from a first sleep state to a second sleep state.

Transitions between the wake state, the NREM state, and the REM state are not random and generally follow an expected pattern. For example, generally a subject transitions from a wake state to a NREM state, then from the NREM state to the REM state. The post-classification component 150 may be configured to recognize these transition patterns, and use a transition probability matrix and emission probabilities for a given state. The post-classification component 150 may act as a verification component of the frame predictions data 142 determined by the sleep state classification component 140. For example, in some cases, the sleep state classification component 140 may determine a first video frame corresponds to a wake state, and a subsequent second video frame corresponds to a REM state. In such cases, the post-classification component 150 may update the sleep state for the first video frame or the second video frame based on knowing that transition from a wake state to a REM state is unlikely especially in the short period of time covered in a video frame. The post-classification component 150 may use the window-based processing of video frames to determine a sleep state for a video frame. In some embodiments, the post-classification component 150 may also take into consideration a duration of a sleep state before transitioning to another sleep state. For example, the post-classification component 150 may determine whether a sleep state for a video frame is accurate, as determined by the sleep state classification component 140, based on how long the NREM state lasts for the subject in the video data 104 before transitioning to the REM state. In some embodiments, the post-classification component 150 may employ various techniques, for example, a statistical model (e.g., a Markov model, a Hidden Markov model, etc.), a probabilistic model, etc. The statistical or probabilistic model may model the dependencies between the sleep states (the wake state, the NREM state and the REM state).

The post-classification component 150 may process the frame predictions data 142 to determine a duration of time of one or more sleep states (a wake state, a NREM state, a REM state) for the subject represented in the video data 104. The post-classification component 150 may process the frame predictions data 142 to determine a frequency of one or more sleep states (a wake state, a NREM state, a REM state) for the subject represented in the video data 104 (a number times a sleep state occurs in the video data 104). The post-classification component 150 may process the frame predictions data 142 to determine a change in one or more sleep states for the subject. The sleep state data 152 may include the duration of time of one or more sleep states for the subject, the frequency of one or more sleep states for the subject, and/or the change in one or more sleep states for the subject.

The post-classification component 150 may output the sleep state data 152, which may be a vector or a matrix including sleep state labels for each video frame of the video data 104. For example, the sleep state data 152 may include a first label "wake state" corresponding to a first video frame, a second label "wake state" corresponding to a second video frame, a third label "NREM state" corresponding to a third video frame, a fourth label "REM state" corresponding to a fourth video frame, etc.

The system(s) 105 may send the sleep state data 152 to the device 102 for display. The sleep state data 152 may be presented as graph data, for example, as shown in FIG. 11A-D.

As described herein, in some embodiments, the automated sleep state system 100 may determine, using the plurality of features (determined by the features extraction component 120), a plurality of body areas of the subject, where each body area corresponds to a video frame of the video data 104, and the automated sleep state system 100 may determine the sleep state data 152 based on changes in the plurality of body areas during the video.

As described herein, in some embodiments, the automated sleep state system 100 may determine, using the plurality of features (determined by the features extraction component 120), a plurality of width-length ratios, where each width-length ratio of the plurality of width-length ratios corresponds to a video frame of the video data 104, and the automated sleep state system 100 may determine the sleep state data 152 based on changes in the plurality of width-length ratios during the video.

In some embodiments, the automated sleep state system 100 may detect a transition from a NREM state to a REM state based on a change in a body area or body shape of the subject, where the change in the body area or body shape may be a result of muscle atonia. Such transition information may be included in the sleep state data 152.

Correlations, which may be used the automated sleep state system 100, between other features derived from the video data 104 and sleep states of the subject are described below in the Examples section.

In some embodiments, the automated sleep state system 100 may be configured to determine a breathing/respiration rate for the subject by processing the video data 104. The automated sleep state system 100 may determine the breathing rate for the subject by processing the plurality of features (determined by the features extraction component 120). In some embodiments, the automated sleep state system 100 may use the breathing rate to determine the sleep state data 152 for the subject. In some embodiments, the automated sleep state system 100 may determine the breathing rate based on frequency domain and/or time domain features determined by the spectral analysis component 130.

Breathing rate for the subject may vary between sleep states, and may be detected using the features derived from the video data 104. For example, the subject body area and/or the width-length ratio may change during a period of time, such that a signal representation (time or frequency) of the body area and/or the width-length ratio may be a consistent signal between 2.5 to 3 Hz. Such signal representation may appear like a ventilatory waveform. The automated sleep state system 100 may process the video data 104 to extract features representing changes in body shape and/or changes in chest size that correlate to/correspond to breathing by the subject. Such changes may be visible in the video, and can be extracted as time domain and frequency domain features.

During a NREM state, the subject may have a particular breathing rate, for example, between 2.5 to 3 Hz. The automated sleep state system 100 may be configured to recognize certain correlations between the breathing rate and the sleep states. For example, a width-length ratio signal may be more prominent/pronounced in a NREM state than a REM state. As a further example, a signal for the width-length ratio may vary more while in a REM state. The foregoing example correlations may be a result of a subject's breathing rate being more varied during the REM state than the NREM state. Another example correlation may be a low frequency noise captured in the width-length ratio signal during a NREM state. Such a correlation may be attributed to the subject's motion/movement to adjust its sleep posture during a NREM state, and the subject may not move during a REM state due to muscle atonia.

At least the width-length ratio signal (and other signals for other features) derived from the video data 104 exemplifies that the video data 104 captures visual motion of the subject's abdomen and/or chest, which can be used to determine a breathing rate of the subject.

Figure 2B:
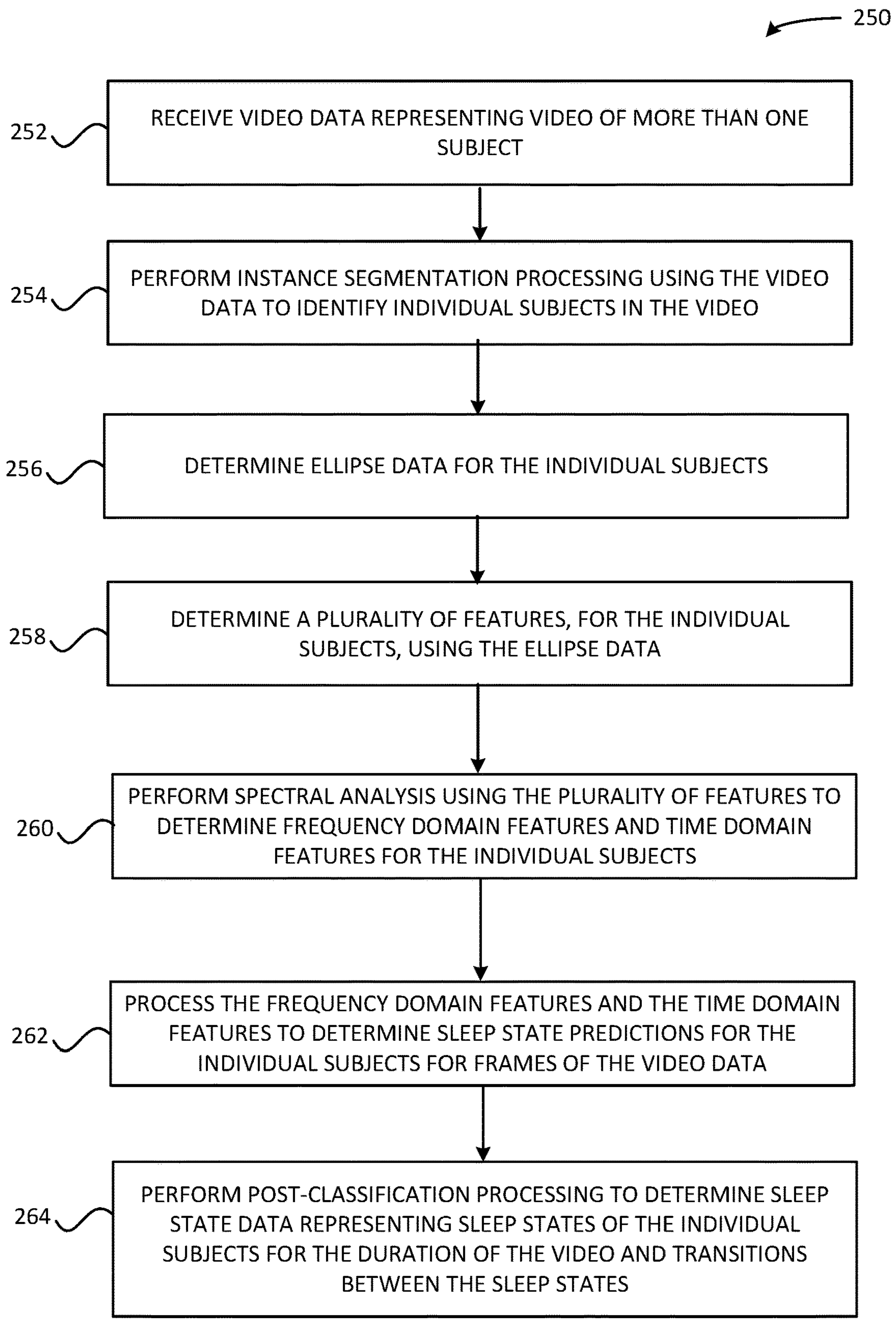
FIG. 2B is a flowchart illustrating a process for determining sleep state data for multiple subjects represented in a video, according to embodiments of the present disclosure.

FIG. 2B is a flowchart illustrating a process 250 for determining sleep state data 152 for multiple subjects represented in a video, according to embodiments of the present disclosure. One or more of the steps of the process 250 may be performed in another order/sequence than shown in FIG. 2B. One or more steps of the process 250 may be performed by the components of the system(s) 105 illustrated in FIG. 1.

Figure 6A:
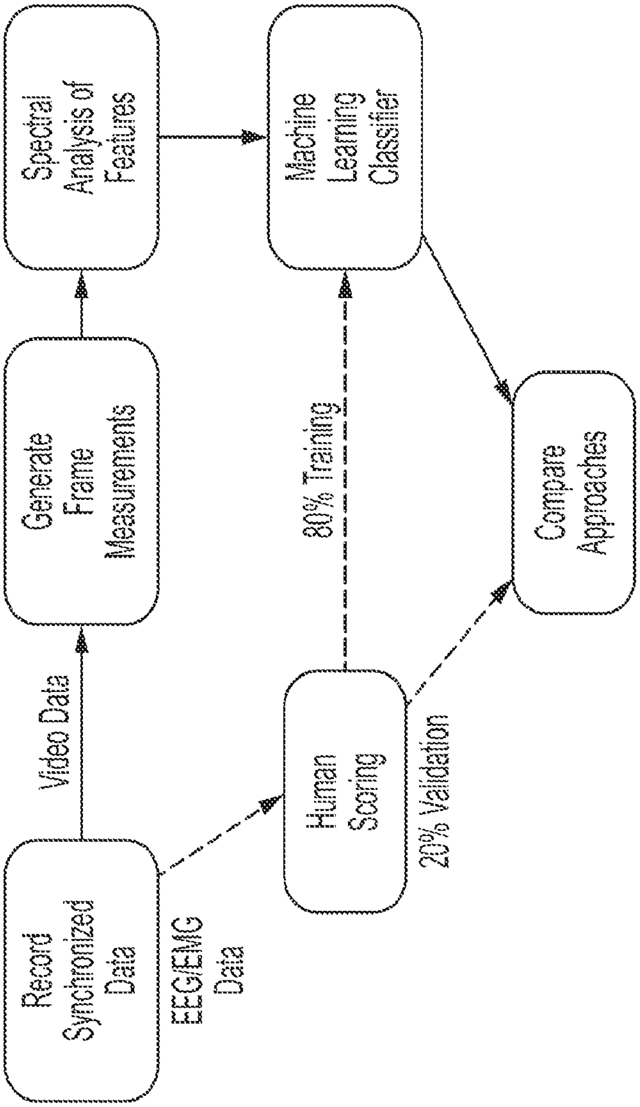
FIG. 6A shows a schematic diagram depicting the organization of data collection, annotation, feature generation, and classifier training according to embodiments of the present disclosure.
Figure 6B:
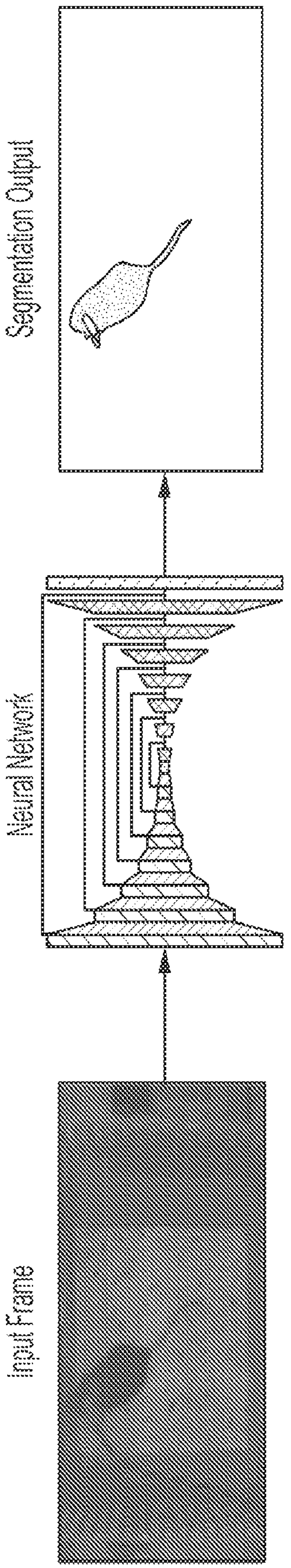
FIG. 6B shows a schematic diagram of frame-level information used for visual features, where a trained neural network was used, according to embodiments of the present disclosure, to produce a segmentation mask of pixels pertaining to the mouse for use in downstream classification.
Figure 6C:
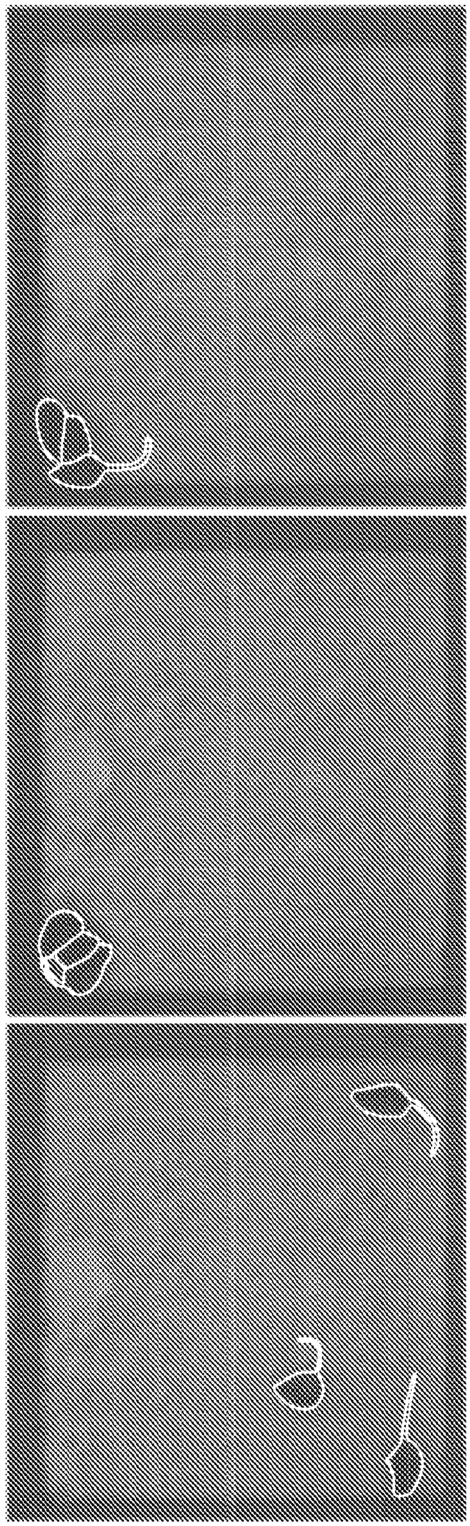
FIG. 6C shows a schematic diagram of multiple frames of a video that includes multiple subjects, where instance segmentation techniques are used, according to embodiments of the present disclosure, to produce segmentation masks for individual subjects, even when they are in close proximity to one another.

At a step 252 of the process 250 shown in FIG. 2B, the system(s) 105 may receive the video data 104 representing video of multiple subjects (e.g., as shown in FIG. 6C).

At a step 254, the segmentation component 110 may perform instance segmentation processing using the video data 104 to identify the individual subjects represented in the video. The segmentation component 110 may employ instance segmentation techniques to process the video data 104 to generate a segmentation masks identifying the individual subjects in the video data 104. The segmentation component 110 may generate a first segmentation mask for a first subject, a second segmentation mask for a second subject, and so on, where the individual segmenation masks may indicate which pixels in the video frame correspond to the respective subject. The segmentation component 110 may also determine which pixels in the video frame correspond to a background/non-subject. The segmentation component 110 may employ one or more machine learning models to process the video data 104 to determine first segmentation data indicating a first set of pixels, of a video frame, corresponding to a first subject, second segmentation data indicating a second set of pixels, of the video frame, corresponding to a second subject, and so on.

The segmentation component 110 may track the respective segmentation masks for individual subjects using a label (e.g., a text label, a numerical label, or other data), such as "subject 1", "subject 2", etc. The segmentation component 110 may assign the respective label to the segmentation masks determined from various video frames of the video data 104, and thus, track the set of pixels corresponding to an individual subject through multiple video frames. The segmentation component 110 may be configured to track an individual subject across multiple video frames even when the subjects move, change positions, change locations, etc. The segmentation component 110 may also be configured to identify the individual subjects when they are in close proximity to one another, for example, as shown in FIG. 6C. In some cases, subjects may prefer to sleep close or near each other, and the instance segmentation techniques are capable of identifying the individual subjects even when this occurs.

The instance segmentation techniques may involve use of computer vision techniques, algorithms, models, etc. Instance segmentation involves identifying each subject instance within an image/video frame, and may involve assigning a label to each pixel of the video frame. Instance segmentation may use object detection techniques to identify all subjects in a video frame, classify individual subjects, and localize each subject instance using a segmentation mask.

In some embodiments, the system(s) 105 may identify and keep track of an individual subject, from the multiple subjects, based on some metrics for the subject, such as, body size, body shape, body/hair color, etc.

At a step 256 of the process 250, the segmentation component 110 may determine ellipse data 112 for the individual subjects using the segmentation masks for the individual subjects. For example, the segmentation component 110 may determine first ellipse data 112 using the first segmentation mask for the first subject, second ellipse data 112 using the second segmentation mask for the second subject, and so on. The segmentation component 110 may determine the ellipse data 112 in a similar manner as described above in relation to the process 200 shown in FIG. 2A.

At a step 258 of the process 250, the features extraction component 120 may determine a plurality of features for the individual subjects using the respective ellipse data 112. The plurality of features may be frame-based features, that is, the plurality of features may be for each individual video frame of the video data 104, and may be provided as the frame features data 122. The features extraction component 120 may determine first frame features data 122 using the first ellipse data 112 and corresponding to the first subject, second frame features data 122 using the second ellipse data 112 and corresponding to the second subject, and so on. The features extraction component 120 may determine the frame features data 122 in a similar manner as described above in relation to the process 200 shown in FIG. 2A.

At a step 260 of the process 250, the spectral analysis component 130 may perform (in a similar manner as described above in relation to the process 200 shown in FIG. 2A) spectral analysis using the plurality of features to determine frequency domain features 132 and time domain features 134 for the individual subjects. The spectral analysis component 130 may determine first frequency domain features 132 for the first subject, second frequency domain features 132 for the second subject, first time domain features 134 for the first subject, second time domain features 134 for the second subject, and so on.

At a step 262 of the process 250, the sleep state classification component 140 may process the respective frequency domain features 132 and the time domain features 134, for an individual subject, to determine sleep predictions for the individual subjects for video frames of the video data 104 (in a similar manner as described above in relation to the process 200 shown in FIG. 2A). For example, the sleep state classification component 140 may determine first frame predictions data 142 for the first subject, second frame predictions data 142 for the second subject, and so on.

At a step 264 of the process 250, the post-classification component 150 may perform post-classification processing (in a similar manner as described above in relation to the process 200 shown in FIG. 2A) to determine the sleep state data 152 representing sleep states of the individual subjects for the duration of the video and transitions between the sleep states. For example, the post-classification component 150 may determine first sleep state data 152 for the first subject, second sleep state data 152 for the second subject, and so on.

Figure 3:
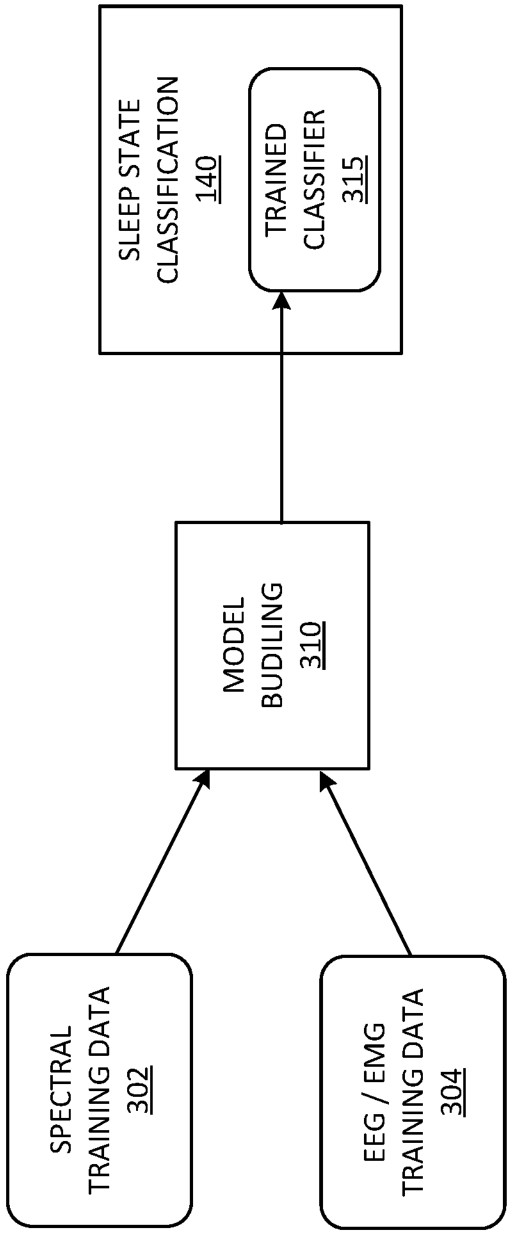
FIG. 3 is a conceptual diagram of a system for training a component for determining sleep state data, according to embodiments of the present disclosure.

In this manner, using instance segmentation techniques, the system(s) 105 may identify multiple subjects in a video, and determine sleep state data for individual subjects using feature data (and other data) corresponding to the respective subjects. By being able to identify each subject, even when they are close together, the system(s) 105 is able to determine sleep states for multiple subjects housed together (i.e. multiple subjects included in the same enclosure). One of the benefits of this is that subjects can be observed in their natural environment, under natural conditions, which may involve co-habiting with another subject. In some cases, other subject behaviors may also be identified/studied based on the co-habitance of the subjects (e.g., affects of co-habitance on sleep states, do the subjects follow the same/similar sleep pattern because of co-habitance, etc.). Another benefit is that sleep state data can be determined for multiple subjects by processing the same/one video, which can reduce the resources (e.g., time, computational resources, etc.) used, as compared to the resources used to process multiple separate videos each representing one subject. FIG. 3 conceptually shows components and data that may be used to configure the sleep state classification component 140 shown in FIG. 1. As described herein, the sleep state classification component 140 may include one or more ML models for processing features derived from the video data 104. The ML model(s) may be trained/configured using various types of training data and training techniques.

In some embodiments, spectral training data 302 may be processed by a model building component 310 to train/configure a trained classifier 315. In some embodiments, the model building component 310 may also process EEG/EMG training data to train/configure the trained classifier 315. The trained classifier 315 may be configured to determine a sleep state label for a video frame based on one or more features corresponding to the video frame.

The spectral training data 302 may include frequency domain signals and/or time domain signals for one or more features of a subject represented in video data to be used for training. Such features may correspond to the features determined by the features extraction component 120. For example, the spectral training data 302 may include a frequency domain signal and/or a time domain signal corresponding to a subject body area during the video. The frequency domain signal and/or the time domain signal may be annotated/labeled with a corresponding sleep state. The spectral training data 302 may include frequency domain signals and/or time domain signals for other features, such as, width-length ratios of the subject, a width of the subject, a length of the subject, a location of the subject, Hu image moments, and other features.

The EEG/EMG training data 304 may be electroencephalography (EEG) data and/or electromyography (EMG) data corresponding to a subject to be used for training/configuring the sleep state classification component 140. The EEG data and/or the EMG data may be annotated/labeled with a corresponding sleep state.

The spectral training data 302 and the EEG/EMG training data 304 may correspond to the same subject's sleep. The model building component 310 may correlate the spectral training data 302 and the EEG/EMG training data 304 to train/configure the trained classifier 315 to identify sleep states from spectral data (frequency domain features and time domain features).

There may be an imbalance in the training dataset due to a subject experiencing more NREM states during sleep than REM states. For training/configured the trained classifier 315, a balanced training dataset may be generated to include same/similar numbers of REM states, NREM states and wake states.

Subjects

Some aspects of the invention include determining sleep state data for a subject. As used herein, a the term "subject" may refer to a human, non-human primate, cow, horse, pig, sheep, goat, dog, cat, pig, bird, rodent, or other suitable vertebrate or invertebrate organism. In certain embodiments of the invention, a subject is a mammal and in certain embodiments of the invention, a subject is a human. In some embodiments, a subject used in method of the invention is a rodent, including but not limited to a: mouse, rat, gerbil, hamster, etc. In some embodiments of the invention, a subject is a normal, healthy subject and in some embodiments, a subject is known to have, at risk of having, or suspected of having a disease or condition. In certain embodiments of the invention, a subject is an animal model for a disease or condition. For, example though not intended to be limiting, in some embodiments of the invention a subject is a mouse that is an animal model for sleep apnea.

As a non-limiting example, a subject assessed with a method and system of the invention may be a subject that has, is suspected of having, and/or is an animal model for a condition such as one or more of: sleep apnea, insomnia, narcolepsy, a brain injury, depression, psychiatric illness, neurodegenerative illness, restless leg syndrome, Alzheimer's disease, Parkinson's disease, a neurological condition capable of altering a sleep state status, and a metabolic disorder or conditions capable of altering a sleep state. A non-limiting example of a metabolic disorder or condition capable of altering a sleep state is a high fat diet. Additional physical conditions may also be assessed using a method of the invention, non-limiting examples of which are obesity, overweight, effects of an administered drug, and/or effects of ingesting alcohol. Additional diseases and conditions can also be assessed using methods of the invention, including but not limited to sleep conditions resulting from chronic disease, drug abuse, injury, etc. . . .

Methods and systems of the invention may also be used to assess a subject or test subject that does not have one or more of sleep apnea, insomnia, narcolepsy, a brain injury, depression, psychiatric illness, neurodegenerative illness, restless leg syndrome, Alzheimer's disease, Parkinson's disease, a neurological condition capable of altering a sleep state status, and a metabolic disorder or conditions capable of altering a sleep state. In some embodiments, methods of the invention are used to assess sleep states in subject without obesity, overweight, alcohol ingestion. Such subject may serve as control subjects and results of assessment with a method of the invention can be used as control data.

In some embodiments of the invention, a subject is a wild-type subject. As used herein the term "wild-type" means to the phenotype and/or genotype of the typical form of a species as it occurs in nature. In certain embodiments of the invention a subject is a non-wild-type subject, for example, a subject with one or more genetic modifications compared to the wild-type genotype and/or phenotype of the subject's species. In some instances, a genotypic/phenotypic difference of a subject compared to wild-type results from a hereditary (germline) mutation or an acquired (somatic) mutation. Factors that may result in a subject exhibiting one or more somatic mutations include but are not limited to: environmental factors, toxins, ultraviolet radiation, a spontaneous error arising in cell division, a teratogenic event such as but not limited to radiation, maternal infection, chemicals, etc.

In certain embodiments of methods of the invention, a subject is a genetically modified organism, also referred to as an engineered subject. An engineered subject may include a pre-selected and/or intentional genetic modification and as such exhibits one or more genotypic and/or phenotypic traits that differ from the traits in a non-engineered subject. In some embodiments of the invention, routine genetic engineering techniques can be used to produce an engineered subject that exhibits genotypic and/or phenotypic differences compared to a non-engineered subject of the species. As a non-limiting example, a genetically engineered mouse in which a functional gene product is missing or is present in the mouse at a reduced level and a method or system of the invention can be used to assess the genetically engineered mouse phenotype, and the results may be compared to results obtained from a control (control results).

In some embodiments of the invention, a subject may be monitored using an automated sleep state determining method or system of the invention and the presence or absence of an sleep disorder or condition can be detected. In certain embodiments of the invention, a test subject that is an animal model of a sleep condition may be used to assess the test subject's response to the condition. In addition, a test subject including but not limited to a test subject that is an animal model of a sleep and/or activity condition may be administered a candidate therapeutic agent or method, monitored using an automated sleep state determining method and/or system of the invention and results can be used to determine an efficacy of the candidate therapeutic agent to treat the condition.

As described elsewhere here, methods and systems of the invention may be configured to determine a sleep state of a subject, regardless of the subject's physical characteristics. In some embodiments of the invention, one or more physical characteristics of a subject may be pre-identified characteristics. For example, though not intended to be limiting, a pre-identified physical characteristic may be one or more of: a body shape, a body size, a coat color, a gender, an age, and a phenotype of a disease or condition.

Controls and Candidate Compound Testing and Screening

Results obtained for a subject using a method or system of the invention can be compared to control results. Methods of the invention can also be used to assess a difference in a phenotype in a subject versus a control. Thus, some aspects of the invention provide methods of determining the presence or absence of a change in one or more sleep states in a subject compared to a control. Some embodiments of the invention include using methods of the invention to identify phenotypic characteristics of a disease or condition and in certain embodiments of the invention automated phenotyping is used to assess an effect of a candidate therapeutic compound on a subject.

Results obtained using a method or system of the invention can be advantageously compared to a control. In some embodiments of the invention one or more subjects can be assessed using a method of the invention followed by retesting the subjects following administration of a candidate therapeutic compound to the subject(s). The terms "subject" and "test subject" may be used herein in relation to a subject that is assessed using a method or system of the invention, and the terms "subject" and "test subject" are used interchangeably herein. In certain embodiments of the invention, a result obtained using a method of the invention to assess a test subject is compared to results obtained from the method performed on other test subjects. In some embodiments of the invention a test subject's results are compared to results of sleep state assessment method performed on the test subject at a different time. In some embodiments of the invention, a result obtained using a method of the invention to assess a test subject is compared to a control result.

As used herein a control result may be a predetermined value, which can take a variety of forms. It can be a single cut-off value, such as a median or mean. It can be established based upon comparative groups, such as subjects that have been assessed using a system or method of the invention under similar conditions as the test subject, wherein the test subject is administered a candidate therapeutic agent and the comparative group has not been administered the candidate therapeutic agent. Another example of comparative groups may include subjects known to have a disease or condition and groups without the disease or condition. Another comparative group may be subjects with a family history of a disease or condition and subjects from a group without such a family history. A predetermined value can be arranged, for example, where a tested population is divided equally (or unequally) into groups based on results of testing. Those skilled in the art are able to select appropriate control groups and values for use in comparative methods of the invention.

A subject assessed using a method or system of the invention may be monitored for the presence or absence of a change in one or more sleep state characteristic that occurs in a test condition versus a control condition. As non-limiting examples, in a subject, a change that occurs may include, but is not limited to one of more sleep state characteristics such as: the time period of a sleep state, an interval of time between two sleep states, a number of one or more sleep states during a period of sleep, a ratio of RM versus NRM sleep states, the period of time prior to entering a sleep state, etc. Methods and systems of the invention can be used with test subjects to assess the effects of a disease or condition of the test subject and can also be used to assess efficacy of candidate therapeutic agents. As a non-limiting example of use of method of the invention to assess the presence or absence of a change in one or more characteristics of sleep states of a test subject as a means to identify efficacy of a candidate therapeutic agent, a test subject known to have a disease or condition that impacts the subject's sleep states is assessed using a method of the invention. The test subject is then administered a candidate therapeutic agent and assessed again using the method. The presence or absence of a change in the test subject's results indicates a presence or absence, respectively, of an effect of the candidate therapeutic agent on the sleep state-impacting disease or condition.

It will be understood that in some embodiments of the invention, a test subject may serve as its own control, for example by being assessed two or more times using a method of the invention and comparing the results obtained at two or more of the different assessments. Methods and systems of the invention can be used to assess progression or regression of a disease or condition in a subject, by identifying and comparing changes in phenotypic characteristics, such as sleep state characteristics in a subject over time using two or more assessments of the subject using an embodiment of a method or system of the invention.

Example Devices and Systems

One or more of components of the automated sleep state system 100 may implement a ML model which may take many forms, including a XgBoost model, a random forest model, a neural network, a support vector Machine, or other models, or a combination of any of these models.

Various machine learning techniques may be used to train and operate models to perform various steps described herein, such as determining segmentation masks, determining ellipse data, determining features data, determining sleep state data, etc. Models may be trained and operated according to various machine learning techniques. Such techniques may include, for example, neural networks (such as deep neural networks and/or recurrent neural networks), inference engines, trained classifiers, etc. Examples of trained classifiers include Support Vector Machines (SVMs), neural networks, decision trees, AdaBoost (short for "Adaptive Boosting") combined with decision trees, and random forests. Focusing on SVM as an example, SVM is a supervised learning model with associated learning algorithms that analyze data and recognize patterns in the data, and which are commonly used for classification and regression analysis. Given a set of training examples, each marked as belonging to one of two categories, an SVM training algorithm builds a model that assigns new examples into one category or the other, making it a non-probabilistic binary linear classifier. More complex SVM models may be built with the training set identifying more than two categories, with the SVM determining which category is most similar to input data. An SVM model may be mapped so that the examples of the separate categories are divided by clear gaps. New examples are then mapped into that same space and predicted to belong to a category based on which side of the gaps they fall on. Classifiers may issue a "score" indicating which category the data most closely matches. The score may provide an indication of how closely the data matches the category.

A neural network may include a number of layers, from an input layer through an output layer. Each layer is configured to take as input a particular type of data and output another type of data. The output from one layer is taken as the input to the next layer. While values for the input data/output data of a particular layer are not known until a neural network is actually operating during runtime, the data describing the neural network describes the structure, parameters, and operations of the layers of the neural network.

One or more of the middle layers of the neural network may also be known as the hidden layer. Each node of the hidden layer is connected to each node in the input layer and each node in the output layer. In the case where the neural network comprises multiple middle networks, each node in a hidden layer will connect to each node in the next higher layer and next lower layer. Each node of the input layer represents a potential input to the neural network and each node of the output layer represents a potential output of the neural network. Each connection from one node to another node in the next layer may be associated with a weight or score. A neural network may output a single output or a weighted set of possible outputs. Different types of neural networks may be used, for example, a recurrent neural network (RNN), a convolutional neural network (CNN), a deep neural network (DNN), a long short-term memory (LSTM), and/or others.

Processing by a neural network is determined by the learned weights on each node input and the structure of the network. Given a particular input, the neural network determines the output one layer at a time until the output layer of the entire network is calculated.

Connection weights may be initially learned by the neural network during training, where given inputs are associated with known outputs. In a set of training data, a variety of training examples are fed into the network. Each example typically sets the weights of the correct connections from input to output to 1 and gives all connections a weight of 0. As examples in the training data are processed by the neural network, an input may be sent to the network and compared with the associated output to determine how the network performance compares to the target performance. Using a training technique, such as back propagation, the weights of the neural network may be updated to reduce errors made by the neural network when processing the training data.

In order to apply the machine learning techniques, the machine learning processes themselves need to be trained. Training a machine learning component such as, in this case, one of the first or second models, requires establishing a "ground truth" for the training examples. In machine learning, the term "ground truth" refers to the accuracy of a training set's classification for supervised learning techniques. Various techniques may be used to train the models including backpropagation, statistical learning, supervised learning, semi-supervised learning, stochastic learning, or other known techniques.

Figure 4:
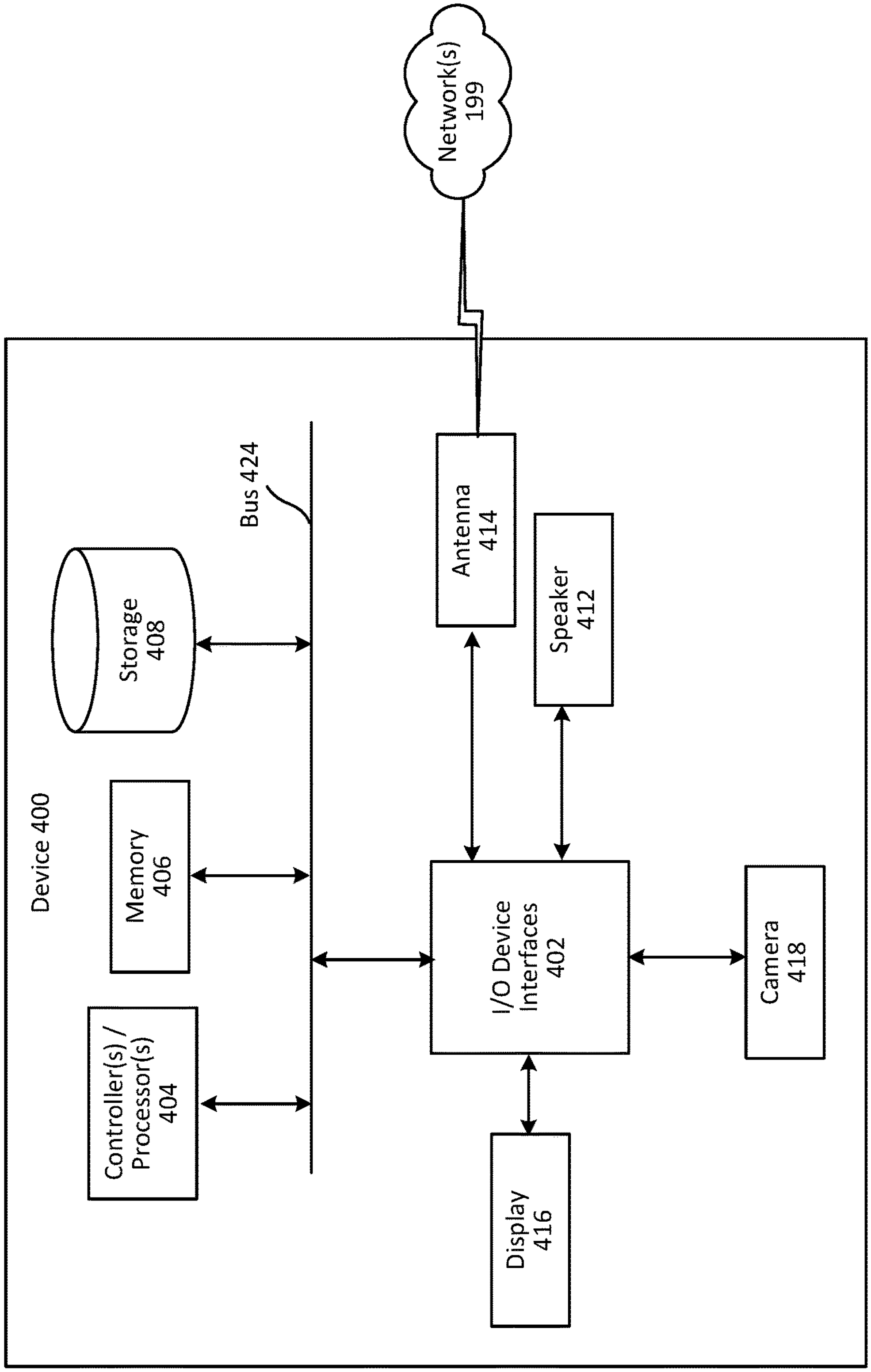
FIG. 4 is a block diagram conceptually illustrating example components of a device according to embodiments of the present disclosure.
Figure 5:
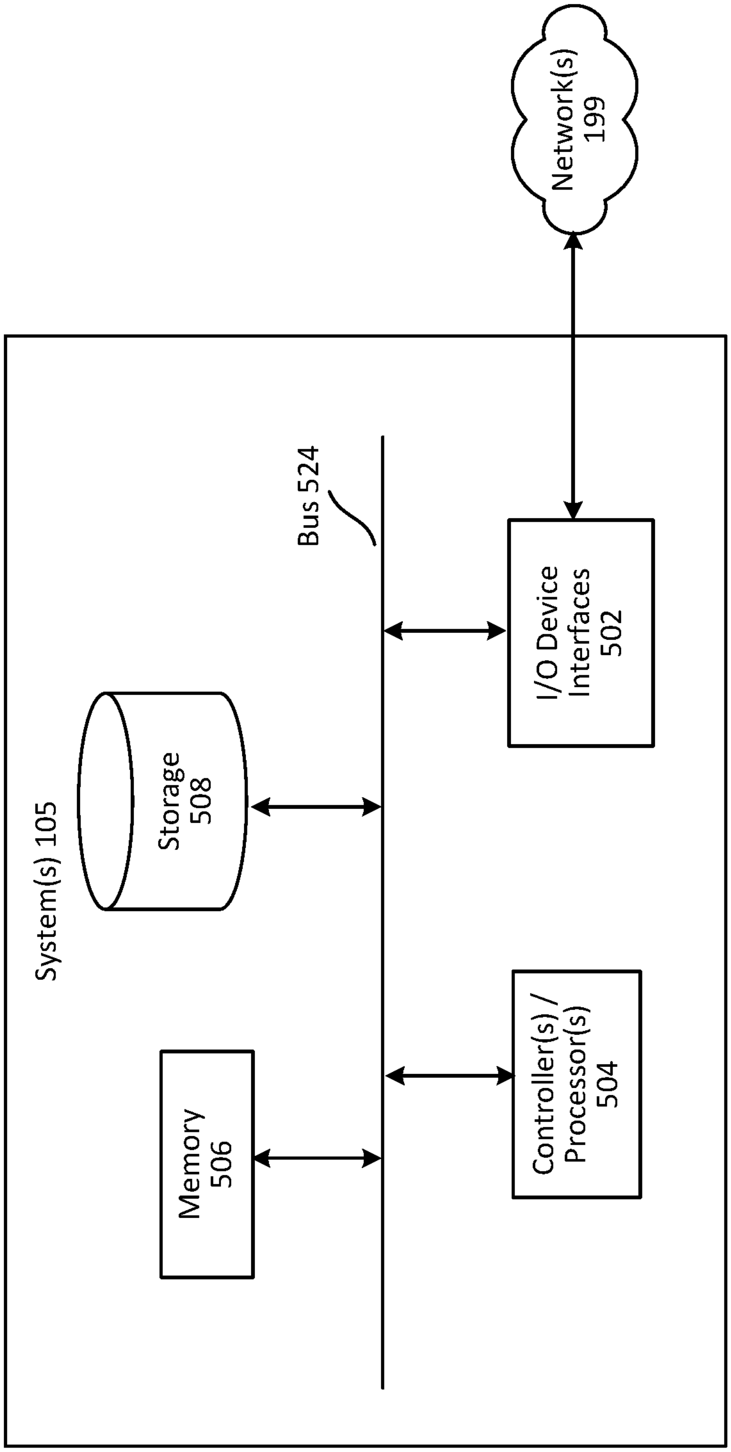
FIG. 5 is a block diagram conceptually illustrating example components of a server according to embodiments of the present disclosure.

FIG. 4 is a block diagram conceptually illustrating a device 400 that may be used with the system. FIG. 5 is a block diagram conceptually illustrating example components of a remote device, such as the system(s) 105, which may assist processing of video data, identifying subject behavior, etc. A system(s) 105 may include one or more servers. A "server" as used herein may refer to a traditional server as understood in a server/client computing structure but may also refer to a number of different computing components that may assist with the operations discussed herein. For example, a server may include one or more physical computing components (such as a rack server) that are connected to other devices/components either physically and/or over a network and is capable of performing computing operations. A server may also include one or more virtual machines that emulates a computer system and is run on one or across multiple devices. A server may also include other combinations of hardware, software, firmware, or the like to perform operations discussed herein. The server(s) may be configured to operate using one or more of a client-server model, a computer bureau model, grid computing techniques, fog computing techniques, mainframe techniques, utility computing techniques, a peer-to-peer model, sandbox techniques, or other computing techniques.

Multiple systems 105 may be included in the overall system of the present disclosure, such as one or more systems 105 for determining ellipse data, one or more system 105 for determining frame features, one or more system 105 for determining frequency domain features, one or more systems 105 for determining time domain features, one or more systems 105 for determining frame-based sleep label predictions, one or more systems 105 determining sleep state data, etc. In operation, each of these systems may include computer-readable and computer-executable instructions that reside on the respective device 105, as will be discussed further below.

Each of these devices (400/105) may include one or more controllers/processors (404/504), which may each include a central processing unit (CPU) for processing data and computer-readable instructions, and a memory (406/506) for storing data and instructions of the respective device. The memories (406/506) may individually include volatile random access memory (RAM), non-volatile read only memory (ROM), non-volatile magnetoresistive memory (MRAM), and/or other types of memory. Each device (400/105) may also include a data storage component (408/508) for storing data and controller/processor-executable instructions. Each data storage component (408/508) may individually include one or more non-volatile storage types such as magnetic storage, optical storage, solid-state storage, etc. Each device (400/105) may also be connected to removable or external non-volatile memory and/or storage (such as a removable memory card, memory key drive, networked storage, etc.) through respective input/output device interfaces (402/502).

Computer instructions for operating each device (400/105) and its various components may be executed by the respective device's controller(s)/processor(s) (404/504), using the memory (406/506) as temporary "working" storage at runtime. A device's computer instructions may be stored in a non-transitory manner in non-volatile memory (406/506), storage (408/508), or an external device(s). Alternatively, some or all of the executable instructions may be embedded in hardware or firmware on the respective device in addition to or instead of software.

Each device (400/105) includes input/output device interfaces (402/502). A variety of components may be connected through the input/output device interfaces (402/502), as will be discussed further below. Additionally, each device (400/105) may include an address/data bus (424/524) for conveying data among components of the respective device. Each component within a device (400/105) may also be directly connected to other components in addition to (or instead of) being connected to other components across the bus (424/524).

Referring to FIG. 4, the device 400 may include input/output device interfaces 402 that connect to a variety of components such as an audio output component such as a speaker 412, a wired headset or a wireless headset (not illustrated), or other component capable of outputting audio. The device 400 may additionally include a display 416 for displaying content. The device 400 may further include a camera 418.

Via antenna(s) 414, the input/output device interfaces 402 may connect to one or more networks 199 via a wireless local area network (WLAN) (such as WiFi) radio, Bluetooth, and/or wireless network radio, such as a radio capable of communication with a wireless communication network such as a Long Term Evolution (LTE) network, WiMAX network, 3G network, 4G network, 5G network, etc. A wired connection such as Ethernet may also be supported. Through the network(s) 199, the system may be distributed across a networked environment. The I/O device interface (402/502) may also include communication components that allow data to be exchanged between devices such as different physical servers in a collection of servers or other components.

The components of the device(s) 400 or the system(s) 105 may include their own dedicated processors, memory, and/or storage. Alternatively, one or more of the components of the device(s) 400, or the system(s) 105 may utilize the I/O interfaces (402/502), processor(s) (404/504), memory (406/506), and/or storage (408/508) of the device(s) 400, or the system(s) 105, respectively.

As noted above, multiple devices may be employed in a single system. In such a multi-device system, each of the devices may include different components for performing different aspects of the system's processing. The multiple devices may include overlapping components. The components of the device 400, and the system(s) 105, as described herein, are illustrative, and may be located as a stand-alone device or may be included, in whole or in part, as a component of a larger device or system.

The concepts disclosed herein may be applied within a number of different devices and computer systems, including, for example, general-purpose computing systems, video/image processing systems, and distributed computing environments.

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of computers and speech processing should recognize that components and process steps described herein may be interchangeable with other components or steps, or combinations of components or steps, and still achieve the benefits and advantages of the present disclosure. Moreover, it should be apparent to one skilled in the art, that the disclosure may be practiced without some or all of the specific details and steps disclosed herein.

Aspects of the disclosed system may be implemented as a computer method or as an article of manufacture such as a memory device or non-transitory computer readable storage medium. The computer readable storage medium may be readable by a computer and may comprise instructions for causing a computer or other device to perform processes described in the present disclosure. The computer readable storage medium may be implemented by a volatile computer memory, non-volatile computer memory, hard drive, solid-state memory, flash drive, removable disk, and/or other media. In addition, components of system may be implemented as in firmware or hardware.

EXAMPLES

Example 1. Development of Mouse Sleep State Classifier Model

Methods

Animal Housing, Surgery, and Experimental Setup

Sleep studies were conducted in 17 C57BL/6J (The Jackson Laboratory, Bar Harbor, ME) male mice. C3H/HeJ (The Jackson Laboratory, Bar Harbor, ME) mice were also imaged without surgery for feature inspection. All mice were obtained at 10-12 weeks of age. All animal studies were performed in accordance with the guidelines published by the National Institutes of Health Guide for the Care and Use of Laboratory Animals and were approved by the University of Pennsylvania Animal Care and Use committee. Study methods were as previously described [Pack, A. I. et al. *Physiol. Genomics.* 28(2): 232-238 (2007); McShane, B. B. et al., *Sleep.* 35(3):433-442 (2012)].

Briefly, mice were individually housed in an open top standard mouse cage (6 by 6 inches). The height of each cage was extended to 12 inches to prevent mice from jumping out of the cage. This design allowed simultaneous assessment of mouse behavior by video and of sleep/wake stages by EG/EMG recording. Animals were fed water and food ad libitum and were in a 12-hour light/dark cycle. During the light phase, the lux level at the bottom of the cage was 80 lux. For EEG recording, four silver ball electrodes were placed in the skull: two frontal and two parietotemporal. For EMG recordings, two silver wires were sutured to the dorsal nuchal muscles. All leads were arranged subcutaneously to the center of the skull and connected to a plastic socket pedestal (Plastics One, Torrington, CT) which was fixed to the skull with dental cement. Electrodes were implanted under general anesthesia. Following surgery, animals were given a 10-day recovery period before recording.

EEG EMG Acquisition

For recording of EEG/EMG, raw signals were read using Grass Gamma Software (Astro-Med, West Warwick, RI) and amplified (20,000×). The signal filter settings for EEG were a low cutoff frequency of 0.1 Hz and a high cutoff frequency of 100 Hz. The settings for EMG were a low cutoff frequency of 10 Hz and a high cutoff frequency of 100 Hz. Recordings were digitized at 256 Hz samples/second/channel.

Video Acquisition

A Raspberry Pi 3 model B (Raspberry Pi Foundation, Cambridge, UK) night vision setup was used to record high quality video data in both day and night conditions. A SainSmart (SainSmart, Las Vegas, NV) infrared night vision surveillance camera was used, accompanied with infrared LEDs to illuminate the scene when visible light was absent. The camera was mounted 18 inches above the floor of the home cage looking down providing a top-down view of the mouse for observation. During the day, video data was in color. During the night, video data was monochromatic. Video was recorded at 1920×1080 pixel resolution and 30 frames per second using v412-ctl capture software. For information on aspects of V412-CTL software see for example: www.kernel.org/doc/html/latest/userspace-api/media/v41/v412.html or alternatively the short version: www.kernel.org/

Video and EEG EMG Data Synchronization

The computer clock time was used to synchronize video and EEG/EMG data. The EEG/EMG data collection computer was used as the source clock. At a known time on the EEG/EMG computer, a visual cue was added to the video. The visual cue typically lasted two to three frames in the video, suggesting that possible error in synchronization could be at most 100 ms. Because EEG/EMG data were analyzed in 10-second (10 s) intervals, any possible error in temporal alignment would be negligible.

EEG/EMG Annotation for Training Data

Twenty-four hours of synchronized video and EEG/EMG data were collected for 17 C57BL/6J male mice from the Jackson Laboratory that were 10-12 weeks old. Both the EEG/EMG data and videos were divided into 10 s epochs, and each epoch was scored by trained scorers and labeled as REM, NREM, or wake stage based on EEG and EMG signals. A total of 17,700 EEG/EMG epochs were scored by expert humans. Among them, 48.3%+/−6.9% of epochs were annotated as wake, 47.6%+/−6.7% as NREM and 4.1%+/−1.2% as REM stage. Additionally, SPINDLE's methods were applied for a second annotation [Miladinović, Đ. et al., *PLOS Comput Biol.* 15, e1006968 (2019)]. Similar to human experts, 52% of epochs were annotated as wake, 44% as NREM, and 4% as REM. Because SPINDLE annotated four-second (4 s) epochs, three sequential epochs were joined to compare to the 10 s epochs and epochs were only compared when the three 4 s epochs did not change. When specific epochs were correlated, the agreement between human annotations and SPINDLE was 92% (89% wake, 95% NREM, 80% REM).

Data Preprocessing

Starting with the video data, a previously described segmentation neural network architecture was applied to produce a mask of the mouse [Webb J. M. and Fu Y-H., *Curr. Opin. Neurobiol.* 69:19-24 (2021)]. Three hundred thirteen frames were annotated to train the segmentation network. A 4×4 diamond dilation followed by a 5×5 diamond erosion filter was applied to the raw predicted segmentation. These routine operations were used to improve segmentation quality. With the predicted segmentation and resulting ellipse fit, a variety of per-frame image measurement signals were extracted from each frame as described in Table 1.

All these measurements (Table 1) were calculated by applying OpenCV contour functions on the neural network predicted segmentation mask. The OpenCV functions used included fitEllipse, contourArea, arcLength, moments, and getHuMoments. For information on OpenCV software see for example, //opencv.org. Using all the measurement signal values within an epoch, a set of 20 frequency and time domain features were derived (Table 2). These were calculated using standard signal processing approaches and can be found in example code [github.com/KumarLabJax/MouseSleep].

Training the Classifier

Due to the inherent dataset imbalance, i.e., many more epochs of NREM compared to REM sleep, an equal number of REM, NREM, and wake epochs were randomly selected to generate a balanced dataset. A cross validation approach was used to evaluate classifier performance. All epochs from 13 animals from the balanced dataset for training were randomly selected and imbalanced data from the remaining four animals was used for testing. The process was repeated ten times to generate a range of accuracy measurements. This approach allowed performance on real imbalanced data to be observed while taking advantage of training a classifier on balanced data.

Prediction Post Processing

A Hidden Markov Model (HMM) approach was applied to integrate larger-scale temporal information to enhance prediction quality. The HMM model can correct erroneous predictions made by a classifier by integrating the probability of sleep state transitions and thus obtain more accurate predicted results. The hidden states of the HMM model are the sleep stages, whereas observables come from the probability vector results from the XgBoost algorithm. The transition matrix was empirically computed from the training set sequence of sleep states, then the Viterbi algorithm [Viterbi A J (April 1967) IEEE Transactions on Information Theory vol. 13(2): 260-269] was applied to infer the sequence of the states given a sequence of the out of bag class votes of the XgBoost. In the instant studies, the transition matrix was a 3 by 3 matrix T={S_ij}, where S_ij represented the transition probability from state S_i to state S_j. T (Table 2).

Classifier Performance Analysis

Performance was evaluated using metrics of accuracy as well as several metrics of classification performance: precision, recall, and F1 score. Precision was defined as the ratio of epochs classified by both the classifier and the human scorer for a given sleep stage to all of the epochs that the classifier assigned as that sleep stages. Recall was defined as the ratio of epochs classified by both the classifier and the human scorer for a given sleep stage to all of the epochs that the human scorer classified as the given sleep stage. F1 combined precision and recall and measured the harmonic mean of recall and precision. The mean and standard deviation of the accuracy and the performance matrix were calculated from 10-fold cross-validation.

Results

Experimental Design

As shown in the schematic diagram of FIG. 6A, a goal of the studies described herein was quantifying the plausibility of using exclusively video data to classify mouse sleep state. An experimental paradigm was designed to leverage the current gold standard of sleep state classification, EEG/EMG recordings, as labels for training and evaluating a visual classifier. Overall, synchronized EEG/EMG and video data was recorded for 17 animals (24 hours per animal). The data were split into 10-second epochs. Each epoch was hand scored by human experts. Concurrently, features from video data which could be used in a machine learning classifier were designed. These features were built on per frame measurements that described the animal's visual appearance in individual video frames (Table 1). Signal processing techniques were then applied to the per frame measurements in order to integrate temporal information and generate a set of features for use in a machine learning classifier (Table 2). Finally, the human labeled dataset was split by holding out individual animals into training and validation dataset (80:20, respectively). Using the training dataset, a machine learning classifier was trained to classify 10-second epochs of video into three states: wake, sleep NREM, and sleep REM. The set of held-out animals was used in the validation dataset to quantify classifier performance. When separating the validation set from the training set, whole animal data was held out to ensure that the classifier generalized well across animals instead of learning to predict well only on the animals it was shown.

TABLE 1

Description of per-frame measurements derived from segmentation and resulting ellipse fit of the segmentation mask of the mouse

| Measurement | Measurement Description |
|---|---|
| m00 | Area |
| Perimeter | Perimeter of the mouse silhouette |
| x | Center x-position of ellipse-fit |

TABLE 1-continued

| Description of per-frame measurements derived from segmentation and resulting ellipse fit of the segmentation mask of the mouse | |
|---|---|
| Measurement | Measurement Description |
| y | Center y-position of ellipse-fit |
| w | Minor axis length for an ellipse-fit |
| l | Major axis length for an ellipse-fit |
| wl_ratio | Width divided by length of minor and major axis of ellipse fit |
| dx | Change in ellipse center x-position |
| dy | Change in ellipse center y-position |
| hu0 | Hu moment 0 |
| hu1 | Hu moment 1 |
| hu2 | Hu moment 2 |
| hu3 | Hu moment 3 |
| hu4 | Hu moment 4 |
| hu5 | Hu moment 5 |
| hu6 | Hu moment 6 |

TABLE 2

Transition probability matrix of sleep stages

| | TO | | |
|---|---|---|---|
| FROM | WAKE | NREM | REM |
| WAKE | 97.0% | 3.0% | 0% |
| NREM | 2.4% | 96.5% | 1.1% |
| REM | 10.1% | 4.4% | 85.6% |

Per Frame Features

Computer vision techniques were applied to extract detailed visual measurements of the mouse in each frame. The first computer vision technique used was segmentation of the pixels pertaining to the mouse versus background pixels (FIG. 6B). A segmentation neural network was trained as an approach that operated well in dynamic and challenging environments such as light and dark conditions as well as the moving bedding seen in the mouse arenas [Webb, J. M. and Fu, Y-H., *Curr. Opin. Neurobiol.* 69: 19-24 (2021)]. Segmentation also allowed for removal of the EEG/EMG cable emanating from the instrumentation on head of each mouse so that it did not affect the visual measurements with information about the motion of the head. The segmentation network predicted pixels that were only the mouse and as such the measurements were only based on mouse motion and not the motion of the wire connected to the mouse's skull. Frames randomly sampled from all videos were annotated to achieve this high-quality segmentation and ellipse fit using a previously described network [Geuther, B. Q. et al., *Commun. Biol.* 2:124 (2019)] (FIG. 6B). The neural network required only 313 annotated frames to achieve good performance segmenting the mouse. Example performance of the segmentation network (not shown) by coloring pixels predicted as not-mouse with red and pixels predicted as mouse as blue on top of the original video. Following the segmentation, 16 measurements from the neural network-predicted segmentation were calculated that described the shape and location of the mouse (Table 1). These included major, minor length, and ratio of the mouse from an ellipse fit that described the mouse shape. The location of the mouse (x, y) and change in x, y (dx, dy) were extracted for the center of the ellipse fit. The area of the segmented mouse (m00), perimeter, and seven Hu image moments that were rotationally invariant (HU0-6) [Scammell, T. E. et al., *Neuron.* 93(4): 747-765 (2017)] were also calculated. Hu image moments are numerical descriptions of the segmentation of the mouse through integration and linear combinations of central image moments [Allada, R. and Siegel, J. M. *Curr. Biol.* 18(15):R670-R679 (2008)].

Time-Frequency Features

Next, those per frame features were used to carry out time- and frequency-based analysis in each 10-second epoch. That analysis allowed integration of time information by applying signal processing techniques. As shown in Table 3, six time domain features (kurtosis, mean, median, standard deviation, max, and min of each signal) and 14 frequency domain features (kurtosis of power spectral density, skewness of power spectral density, mean power spectral density for 0.1-1 Hz, 1-3 Hz, 3-5 Hz, 5-8 Hz, 8-15 Hz, total power spectral density, max, min, average, and standard deviation of power spectral density) were extracted for each per frame feature in an epoch, resulting in 320 total features (16 measurements×20 time-frequency features) for each 10-second epoch.

TABLE 3

Time and frequency features extracted from the per frame measurements in Table 1.

| LABEL | DESCRIPTION | DOMAIN | FEATURE # |
|---|---|---|---|
| k | Kurtosis of raw signal | Time domain | 1 |
| k_psd | Kurtosis of power spectral density | Freq. domain | 2 |
| s_psd | Skewness of power spectral density | Freq. domain | 3 |
| MPL_1 | Mean power spectral density (0.1-1 HZ) | Freq. domain | 4 |
| MPL_3 | Mean power spectral density (1-3 HZ) | Freq. domain | 5 |
| MPL_5 | Mean power spectral density (3-5 HZ) | Freq. domain | 6 |
| MPL_8 | Mean power spectral density (5-8 HZ) | Freq. domain | 7 |
| MPL_15 | Mean power spectral density (8-15 HZ) | Freq. domain | 8 |
| Tot_PSD | Total power spectral density | Freq. domain | 9 |
| Max_PSD | Max power spectral density | Freq. domain | 10 |
| Min_PSD | Min power spectral density | Freq. domain | 11 |
| Ave_PSD | Average power spectral density | Freq. domain | 12 |
| Std_PSD | Standard deviation of power spectral density | Freq. domain | 13 |
| Ave_Signal | Average raw signal | Time domain | 14 |
| Std_Signal | Standard deviation of raw signal | Time domain | 15 |
| Max_Signal | Max raw signal | Time domain | 16 |
| Min_Signal | Max raw signal | Time domain | 17 |
| TOP_SIGNAL | Frequency that corresponds to MAX_PSD | Freq. domain | 18 |
| MED_SIGNAL | Median raw signal | Time domain | 19 |
| MED_PSD | Median power spectral density | Freq. domain | 20 |

Figure 7A:
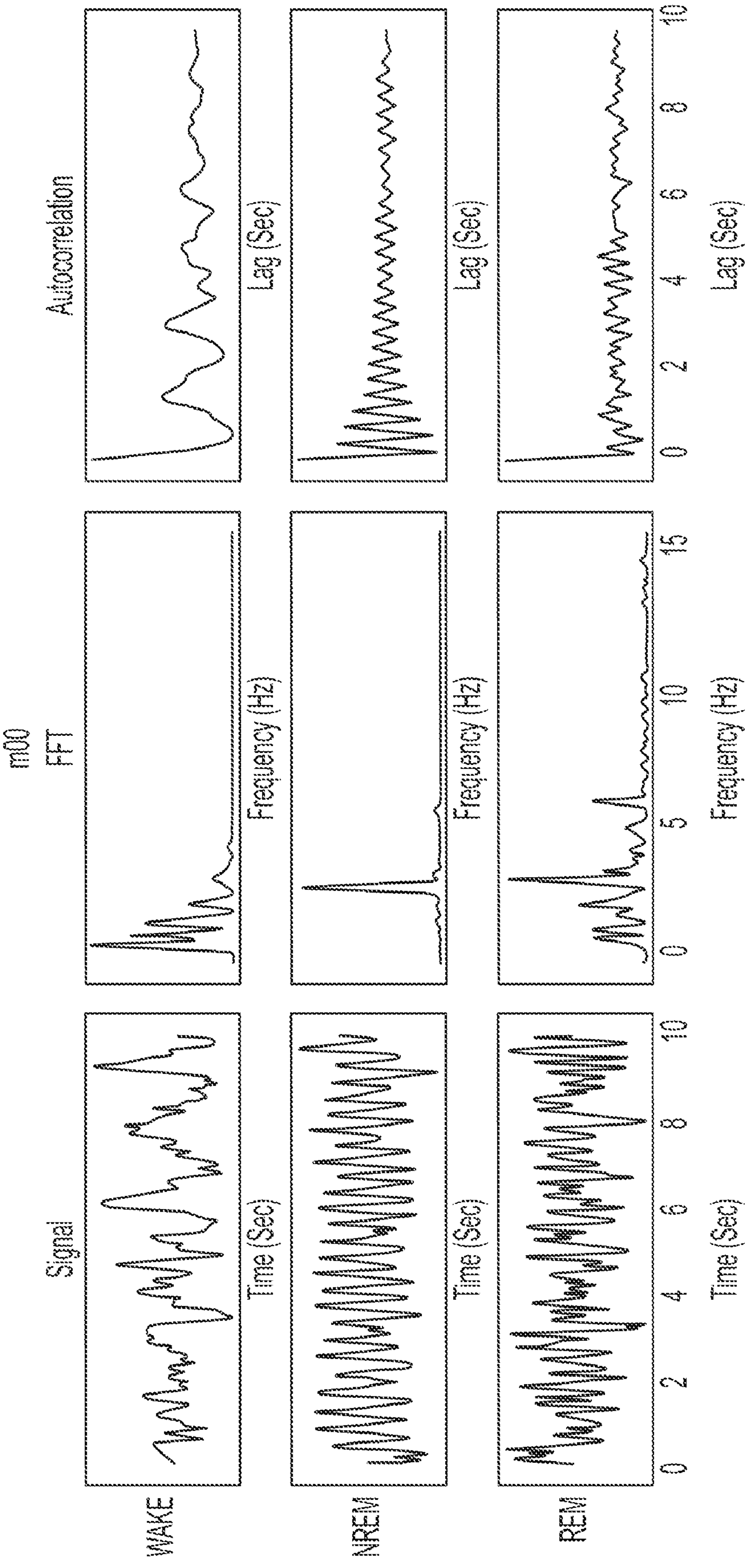
FIG. 7A presents exemplary graphs of selected signals in time and frequency domain within one epoch, that show m00 (area of the segmentation mask) for the wake, NREM, REM states (leftmost column); the FFT of the corresponding signals (middle column); and the autocorrelation of the signals (rightmost column).
Figure 7B:
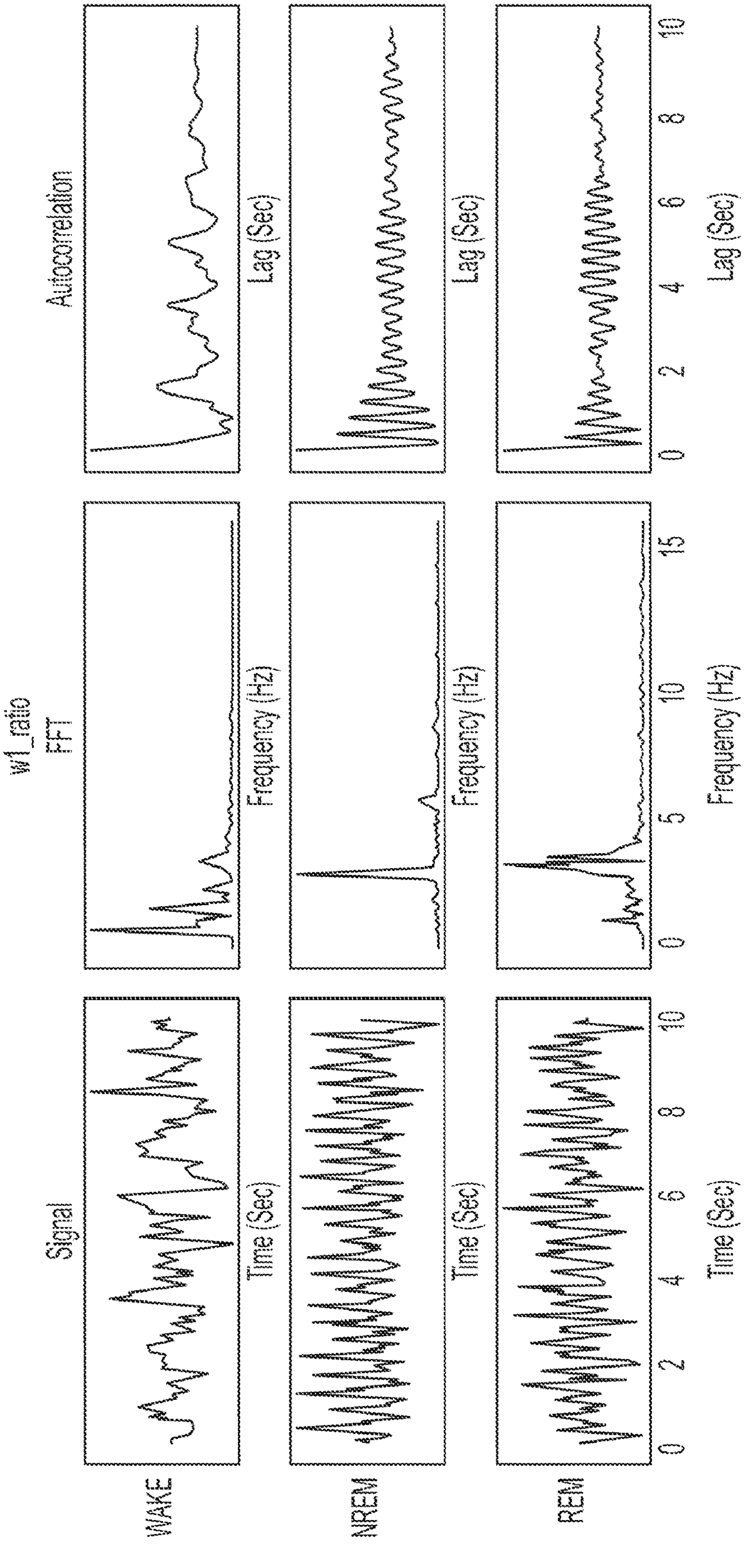
FIG. 7B presents exemplary graphs of selected signals in time and frequency domain within one epoch, that show the wl_ratio in time and frequency domain, similar to FIG. 6A.

These spectral window features were visually inspected to determine if they varied between wake, REM, and NREM states. FIG. 7A-B shows representative epoch examples of m00 (area, FIG. 7A) and wl_ratio (width-length ratio of ellipse major and minor axis, FIG. 7B) features that varied in time and frequency domain for wake, NREM, and REM states. The raw signals for m00 and wl_ratio showed clear oscillation in NREM and REM states (left panels, FIG. 7A and FIG. 7B,) which can be seen in the FFT (middle panels, FIG. 7A and FIG. 7B,) and autocorrelation (right panels, FIG. 7A and FIG. 7B). A single dominant frequency was present in NREM epochs and a wider peak in REM. Additionally, the FFT peak frequency varied slightly between NREM (2.6 Hz) and REM (2.9 Hz) and in general more regular and consistent oscillation was observed in NREM epochs than in REM epochs. Thus, an initial examination of the features revealed differences between the sleep states and provided confidence that useful metrics were encoded in the features for use in a visual sleep classifier.

Breathing Rate

Figure 8A:
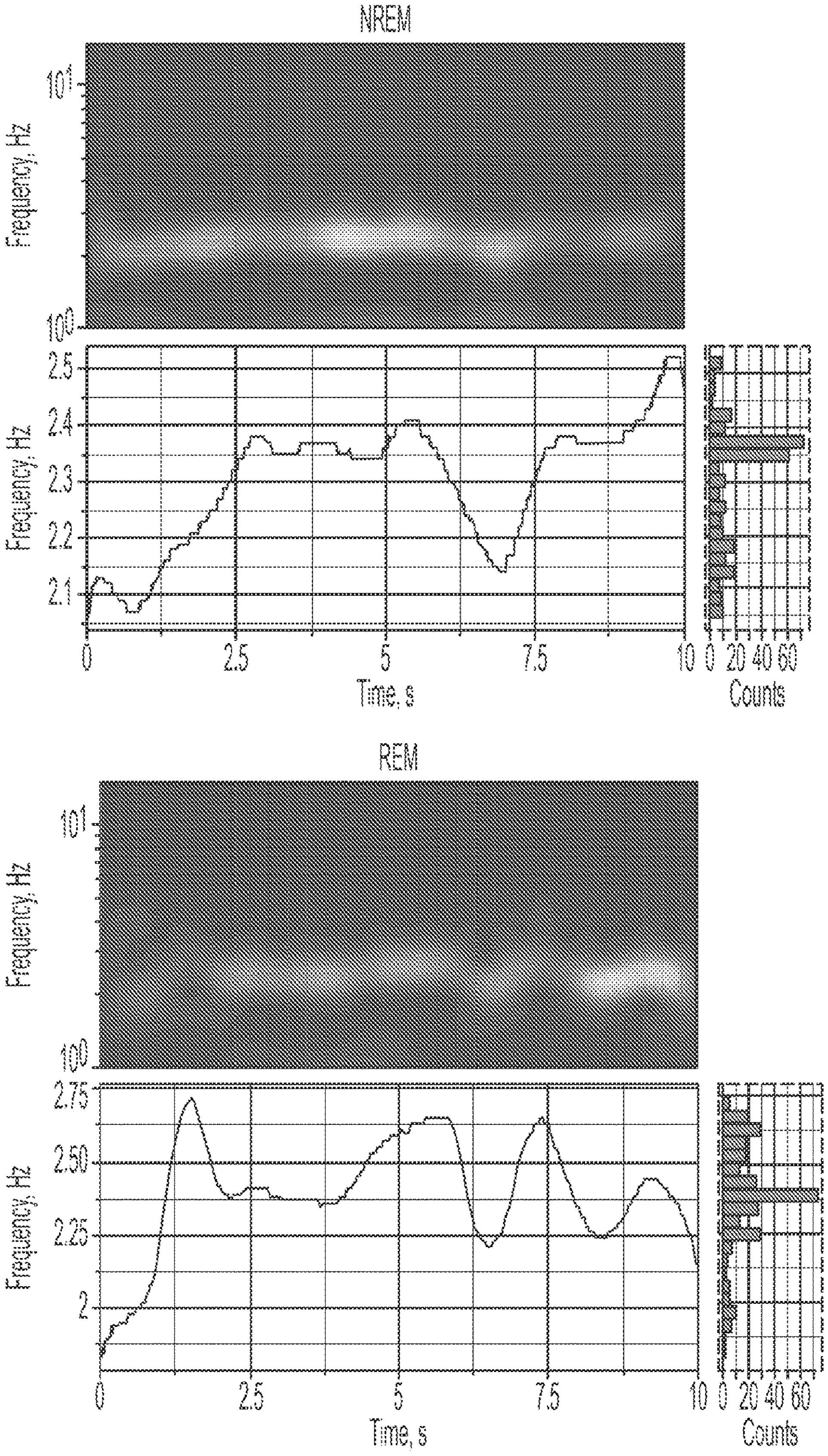
FIG. 8A-B presents plots depicting breathing signal extraction from video.
Figure 8B:
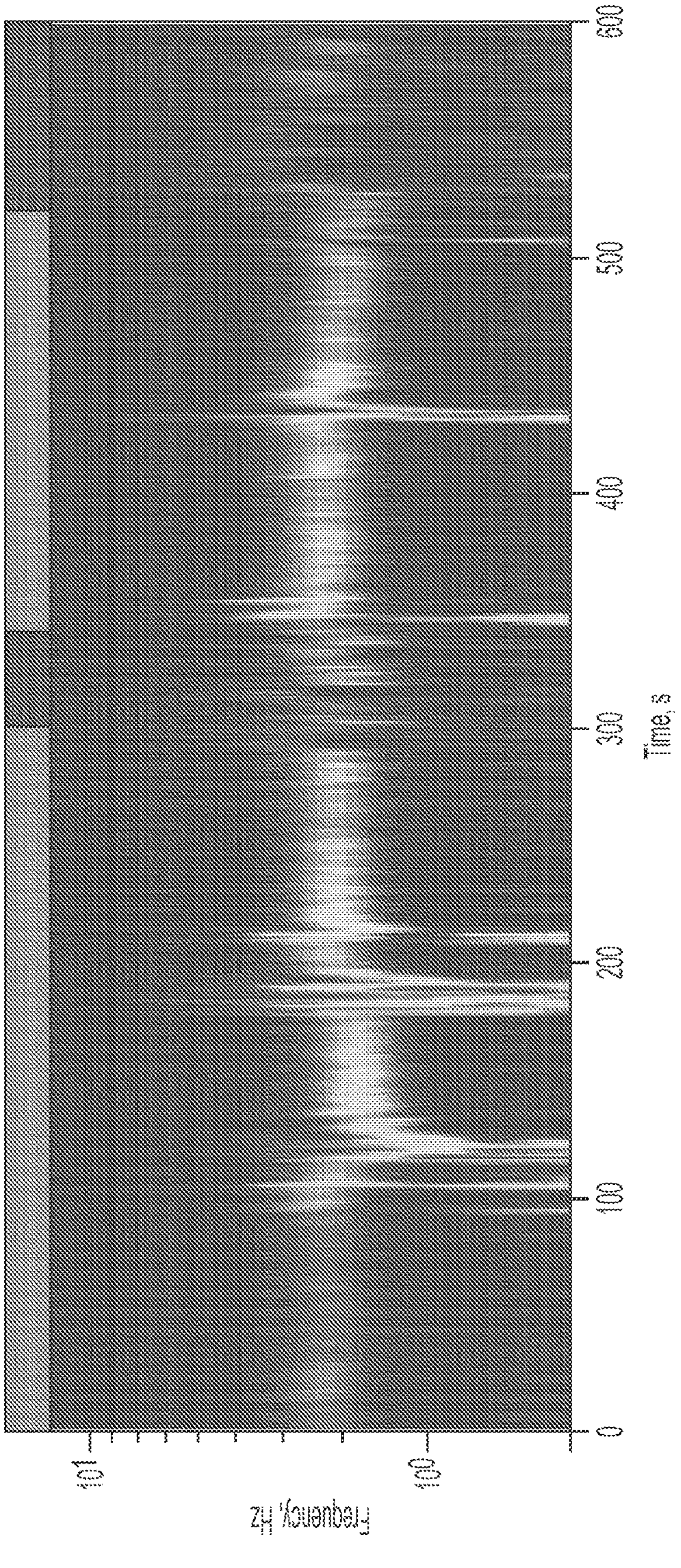

Previous work in both humans and rodents has demonstrated that breathing and movement varies between sleep stages [Stradling, J. R. et al., *Thorax.* 40(5):364-370 (1985); Gould, G. A. et al., *Am. Rev Respir. Dis.* 138(4): 874-877 (1988); Douglas, N.J. et al., *Thorax.* 37(11):840-844 (1982); Kirjavainen, T. et al., *J. Sleep. Res.* 5(3); 186-194 (1996); Friedman, L. et al., *J. Appl. Physiol.* 97(5): 1787-1795 (2004)]. In examining m00 and wl_ratio features, a consistent signal was discovered between 2.5-3 Hz that appeared as a ventilatory waveform (FIGS. 7A-7B). An examination of the video revealed that changes in body shape and changes in chest size due to breathing were visible and may have been captured by the time frequency features. To visualize this signal, continuous wavelet transform (CWT) spectrogram was performed for the wl_ratio feature (FIG. 8A, top panels). To summarize data from these CWT spectrograms, the dominant signal in the CWT was identified (FIG. 8A, respective lower left panels), and a histogram of dominant frequencies in the signal (FIG. 8A, respective lower right panels) was plotted. The mean and variance of the frequencies contained in the dominant signal were calculated from the corresponding histogram. Previous work has demonstrated that C57BL/6J mice have a breathing rate of 2.5-3 Hz during NREM state [Friedman, L. et al., *J. Appl. Physiol.* 97(5): 1787-1795 (2004); Fleury Curado, T. et al., *Sleep.* 41(8):zsy089 (2018)]. Examination of a long bout of sleeping (10 minutes), which included both REM and NREM, showed that the wl_ratio signal was more prominent in NREM than REM, although it was clearly present in both (FIG. 8B). Additionally, the signal varied more within the 2.5-3.0 Hz range while in the REM state, because the REM state caused higher and more variable breathing rate than the NREM state. Low frequency noise in this signal in the NREM state due to larger motion of the mouse, such as adjusting its sleeping posture, was also observed. This suggested that the wl_ratio signal was capturing the visual motion of the mouse abdomen.

Breathing Rate Validation

Figure 9A:
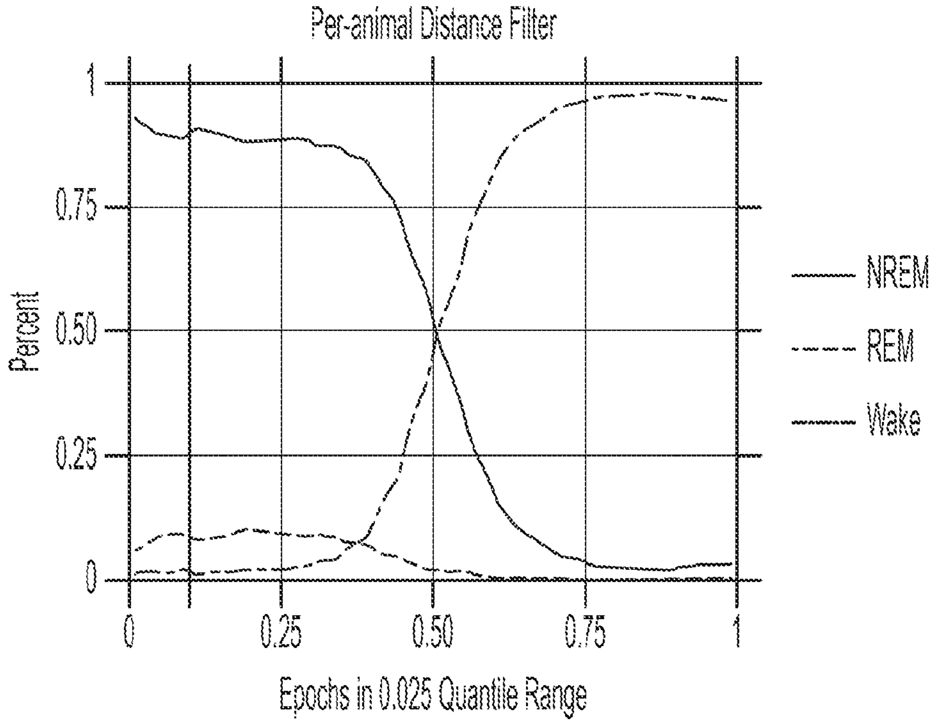
FIG. 9A-C presents graphs illustrating validation of breathing signal in video data for wl_ratio measurement.
Figure 9B:
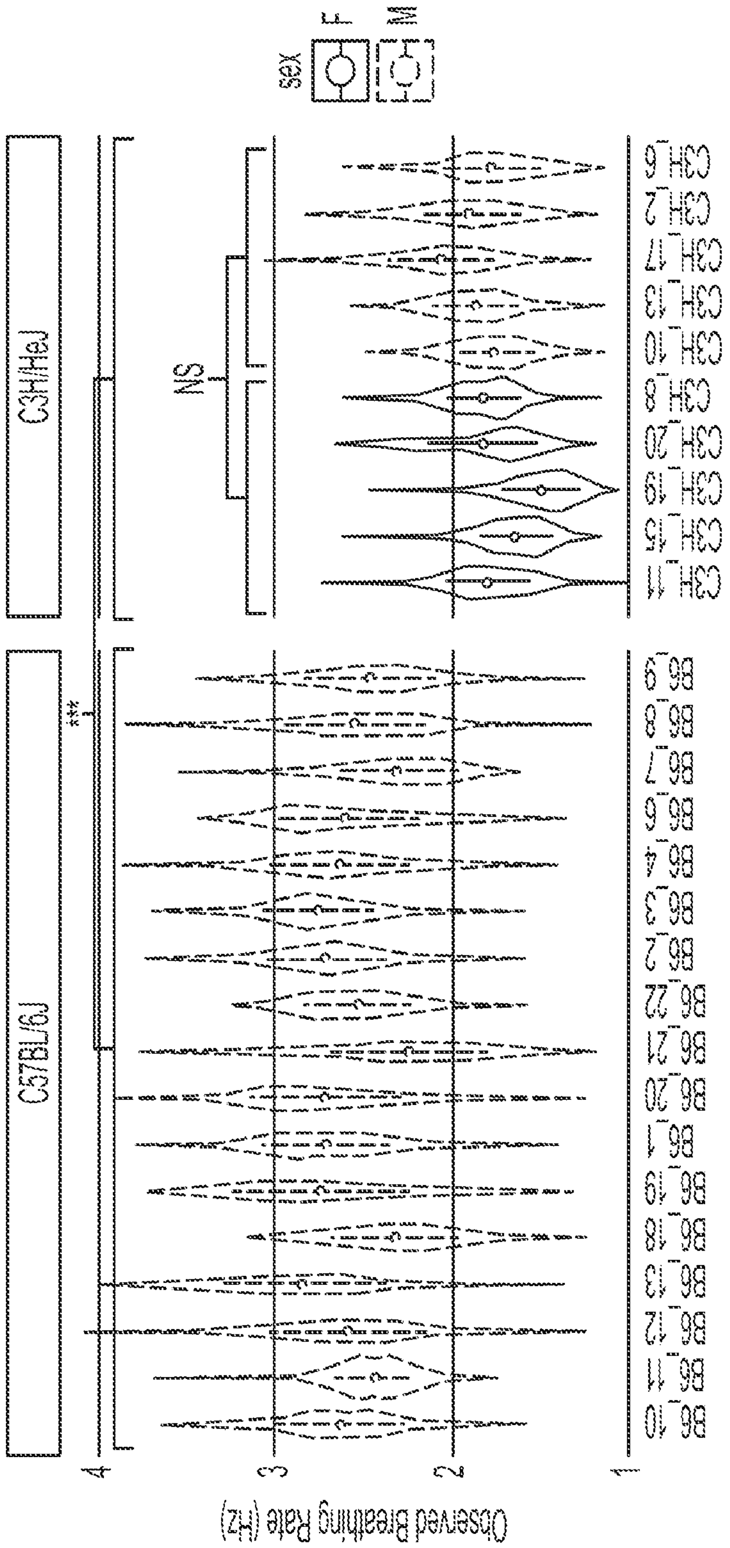

In order to confirm that the signal observed in REM and NREM epochs for m00 and wl_ratio features was abdomen motion and correlated with breathing rate, a genetic validation test was performed. C3H/HeJ mice had previously been demonstrated to have a wake breathing frequency approximately 30% less than that of C57BL/6J mice, ranging from 4.5 vs 3.18 Hz [Berndt. A. et al., *Physiol. Genomics.* 43(1): 1-11 (2011)], 3.01 vs 2.27 Hz [Groeben, H. et al., *Br. J. Anaesth.* 91(4):541-545 (2003)], and 2.68 vs 1.88 Hz [Vium, Inc., Breathing Rate Changes Monitored Non-Invasively 24/7. (2019)] for C57BL/6J and C3H/HeJ, respectively. Un-instrumented C3H/HeJ mice (5 male, 5 female) were video recorded, and the classical sleep/wake heuristic of movement (distance traveled) [Pack, A. I. et al. *Physiol. Genomics.* 28(2):232-238 (2007)] was applied to identify sleep epochs. Epochs were conservatively selected within the lowest 10% quantile for motion. Annotated C57BL/6J EEG/EMG data was used to confirm that the movement-based cutoff was able to accurately identify sleep bouts. Using the EEG/EMG annotated data for the C57BL/6J mice, this cutoff was found to primarily identify NREM and REM epochs (FIG. 9A). Epochs selected in the annotated data consisted of 90.2% NREM, 8.1% REM, and 1.7% wake epochs. Thus, as expected, this mobility-based cutoff method correctly distinguished between sleep/wake and not REM/NREM. From these low motion sleep epochs, the mean value of the dominant frequency in the wl_ratio signal was calculated. This measurement was selected due to its sensitivity to chest area motion. The distribution of the mean dominant frequency for each animal was plotted and consistent distribution was observed between animals. For instance, C57BL/6J animals had an oscillation range from mean frequency of 2.2 to 2.8 Hz, while C3H/HeJ animals ranged from 1.5 to 2.0 Hz, in which C3H/HeJ breathing rates were approximately 30% less than those of C57BL/6J. This was a statistically significant difference between the two strains, i.e., C57BL/6J and C3H/HeJ ($p<0.001$, FIG. 9B) and similar in range to previously reports [Berndt, A. et al., *Physiol. Genomics.* 43(1): 1-11 (2011); Groeben, H. et al., *Br. J. Anaesth.* 91(4):541-545 (2003); Vium, Inc., Breathing Rate Changes Monitored Non-Invasively 24/7. (2019)]. Thus, using this genetic validation method, it was concluded that the observed signal strongly correlated with breathing rate.

Figure 9C:
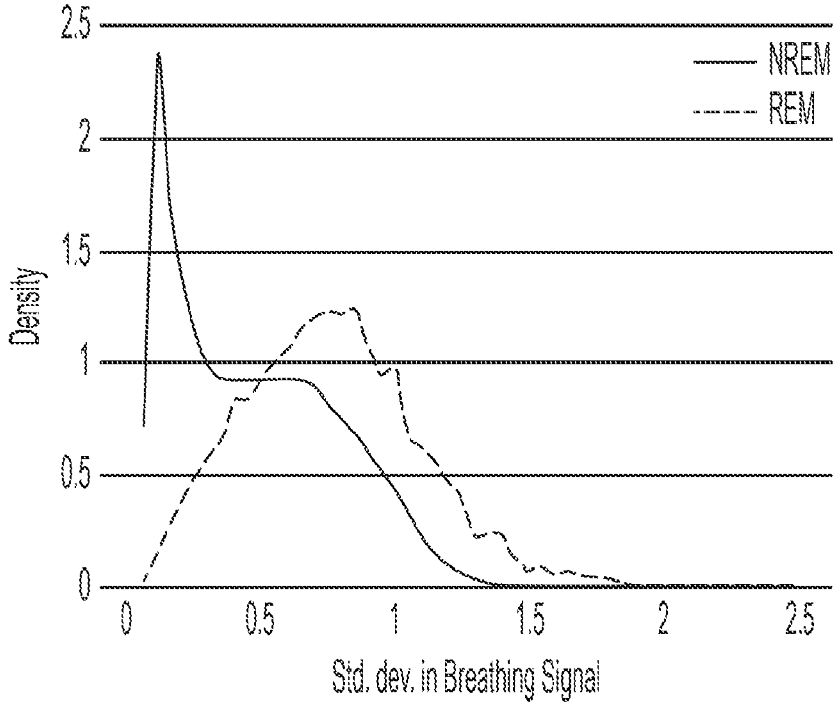
Figure 9D:
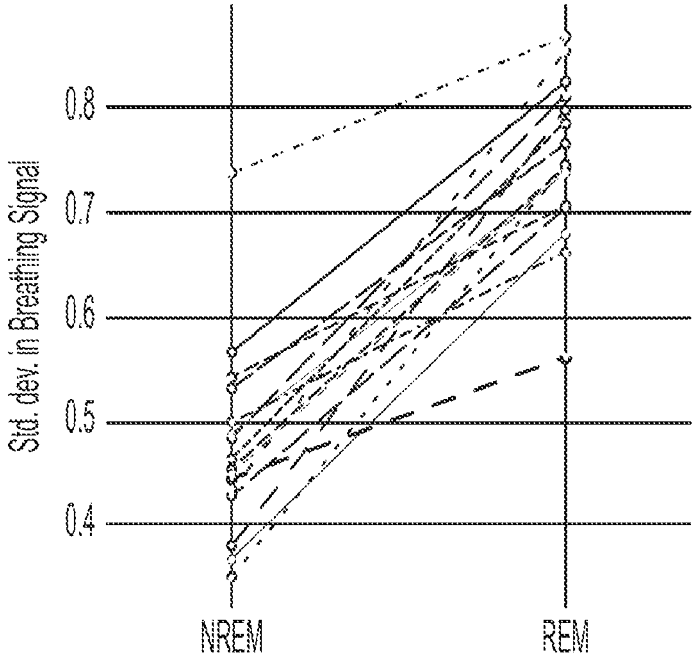
FIG. 9D shows that that increase in standard deviation was consistent across all animals.

In addition to overall changes in breathing frequency due to genetics, breathing during sleep has been shown to be more organized and with less variance during NREM than REM in both humans and rodents [Mang, G. M. et al., *Sleep.* 37(8): 1383-1392 (2014): Terzano, M. G. et al., *Sleep.* 8(2): 137-145 (1985)]. It was hypothesized that the detected breathing signal would show greater variation in REM epochs than in NREM epochs. EEG/EEG annotated C57BL/6J data was examined to determine whether there were changes in variation of CWT peak signal in epochs across REM and NREM states. Using only the C57BL/6J data, epochs were partitioned by NREM and REM states and variation in the CWT peak signal was observed (FIG. 9C). NREM states showed a smaller standard deviation of this signal while the REM state had a wider and higher peak. The NREM state appeared to comprise multiple distributions, possibly indicating sub-divisions of the NREM sleep state [Katsageorgiou, V-M. et al., *PLOS Biol.* 16(5):e2003663 (2018)]. To confirm that this odd shape of the NREM distribution was not an artifact of combining data from multiple animals, data was plotted for each animal and each animal showed increases in standard deviation from NREM to REM state (FIG. 9D). Individual animals also showed this long-tailed NREM distribution. Both of these experiments indicated that the observed signals were breathing rate signals. These results suggested good classifier performance.

Classification

Finally, a machine learning classifier was trained to predict sleep state using the 320 visual features. For validation, all data from an animal was held out to avoid any bias that might be introduced by correlated data within a video. For calculation of training and test accuracy, 10-fold cross-validation was performed by shuffling which animals were held out. A balanced dataset was created as described in Materials and Methods above herein and multiple classification algorithms were compared, including XgBoost, Random Forest, MLP, logistic regression, and SVD. Performances were observed to vary widely among classifiers (Table 4). XgBoost and random forest both achieved good accuracies in the held-out test data. However, the random forest algorithm achieved 100% training accuracy, indicating that it overfit the training data. Overall, the best performing algorithm was the XgBoost classifier.

TABLE 4

Comparison of classifier model performance on dataset used for model construction (training accuracy) with performance on examples the model had not seen (test accuracy).

| Classifier | Training Accuracy | Test Accuracy |
|---|---|---|
| XGBOOST | 0.875 | 0.852 |
| RANDOM FOREST | 1.000 | 0.857 |
| NEURAL NETWORK | 0.635 | 0.696 |
| SVM | 0.597 | 0.564 |

Transitions between wake, NREM, and REM states are not random and generally follow expected patterns. For instance, wake generally transitions to NREM which then transitions to REM sleep. The hidden Markov model is an ideal candidate to model the dependencies between the sleep states. The transition probability matrix and the emission probabilities in a given state are learned using the training data. It was observed that by adding HMM model, the overall classifier accuracy improved by 7% (FIG. 10A, +HMM) from 0.839+/−0.022 to 0.906+/−0.021.

Figure 10A:
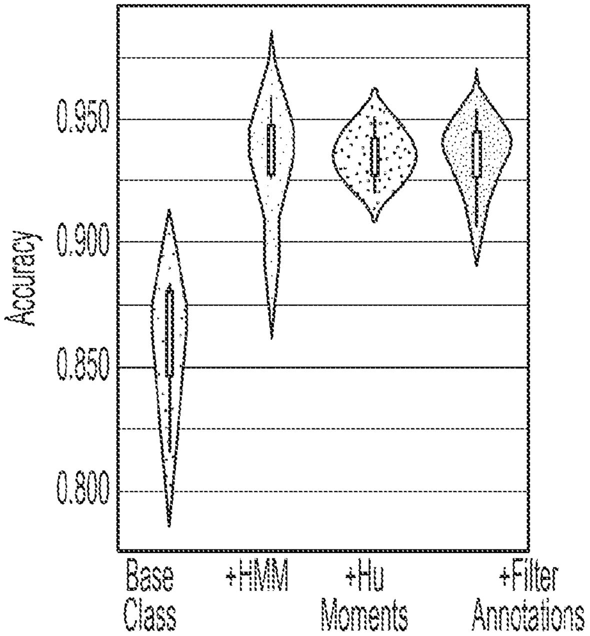
FIG. 10A-D presents graphs and tables illustrating classifier performance metrics.

To enhance classifier performance, Hu moment measurements were adopted from segmentation for inclusion in input features for classification [Hu, M-K. *IRE Trans Inf Theory.* 8(2): 179-187 (1962)]. These image moments were numerical descriptions of the segmentation of the mouse though integration and linear combinations of central image moments. The addition of Hu moment features achieved a slight increase in overall accuracy and increased classifier robustness through decreased variation in cross validation performance (FIG. 10A, +Hu Moments) from 0.906+/−0.021 to 0.913+/−0.019. Even though the EEG/EMG scoring was performed by human trained experts, there is often disagreement between trained annotators [Pack, A. I. et al. *Physiol. Genomics.* 28(2):232-238 (2007)]. Indeed, two experts only generally agreed between 88-94% of the time for REM and NREM [Pack, A. I. et al. *Physiol. Genomics.* 28(2):232-238 (2007)]. A recently published machine learning method was used to score the EEG/EMG data to compliment data from human scorers [Miladinović, Đ. et al., *PLOS Comput. Biol.* 15(4):e1006968 (2019)]. SPINDLE annotations and human annotations were compared, and were found to agree in 92% of all epochs. Only epochs in which both the human and machine-based method agreed were then used as labels for visual classifier training. Classifier training using only epochs where SPINDLE and humans agreed added an additional 1% increase in accuracy (FIG. 10A, +Filter Annotations). Thus, the final classifier achieved a three-state classification accuracy of 0.92+/−0.05.

Figure 10B:
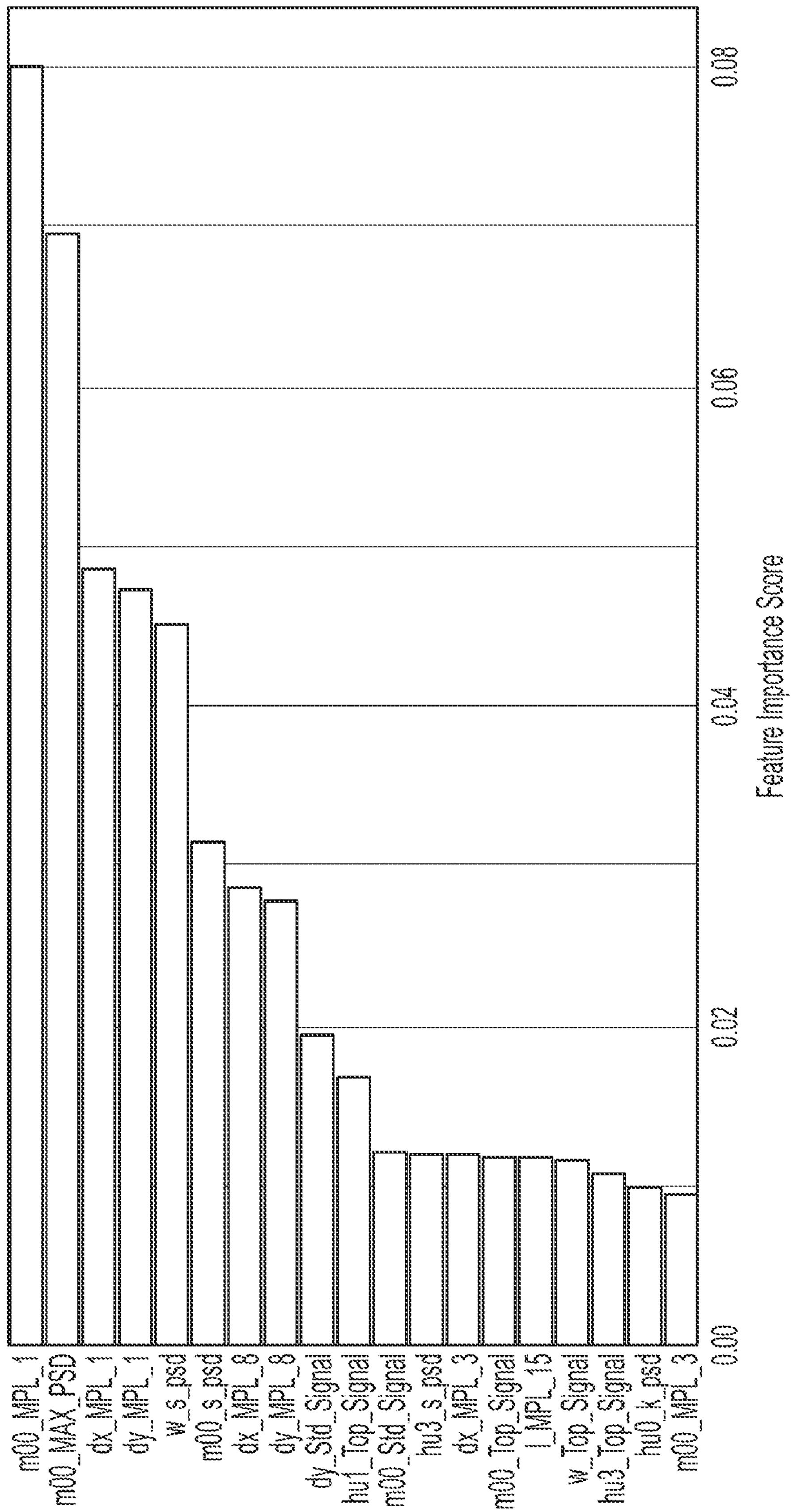

The classification features used were investigated to determine which were most important; area of the mouse and motion measurements were identified as the most important features (FIG. 10B). Though not intended to be limiting, it is thought that this result was observed because motion is the only feature used in binary sleep-wake classification algorithms. Additionally, three of the top five features were low frequency (0.1-1.0 Hz) power spectral densities (FIG. 7A and FIG. 7B, FFT column). Furthermore, it was also observed that wake epochs had the most power in low frequencies, REM had low power in low frequencies, and NREM had the least power in low frequency signals.

Figures 10C, 10D:
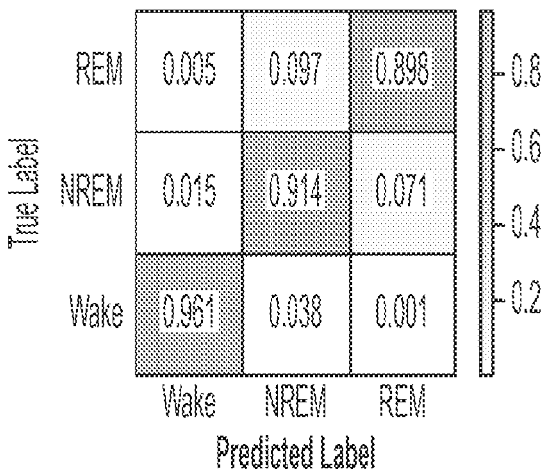

Good performance was observed using the highest performing classifier (FIG. 10C). Rows in the matrix shown in FIG. 10C represent sleep states assigned by a human scorer, while columns represent stages assigned by the classifier. Wake had the highest accuracies of the classes at 96.1% accuracy. By observing the off-diagonals of the matrix, the classifier performed better at distinguishing wake from either sleep states than between the sleep states, showing that distinguishing REM from NREM was a difficult task.

An average of 0.92+/−0.05 overall accuracy was achieved in the final classifier. The prediction accuracy for wake stage was 0.97+/−0.01, with an average precision recall rate of 0.98. The prediction accuracy for NREM stage was 0.92+/0.04, with an average precision recall rate of 0.93. The prediction accuracy for REM stage was around 0.88+/−0.05, with an average precision recall rate of 0.535. The lower precision recall rate for REM was due to a very small percentage of epochs that were labeled as REM stage (4%).

In addition to the prediction accuracy, performance metrics including precision, recall, and F1-score were measured to evaluate the model (FIG. 10D) from the 10-fold cross validation. Given the imbalanced data, precision-recall were better metrics for classifier performance [Powers, D. M. W., *J. Mach. Learn. Technol.* 2(1): 37-63 (2011) ArXiv: 2010.16061; Saito, T, and Rehmsmeier, M. *PLOS ONE.* 10(3):e0118432 (2015)]. Precision measured the proportion of positive items that was correctly predicted, while recall measured the proportion of actual positives that was identified correctly. F1 score was the weighted average of precision and recall.

$$\text{Precision} = \frac{TP}{TP + FP}$$

$$\text{Recall} = \frac{TP}{TP + FN}$$

$$F1 \text{ score} = \frac{2 * (\text{Recall} * \text{Precision})}{\text{Recall} + \text{Precision}}$$

TP, TN, FP, and FN are true positives, true negatives, false positives, and false negatives respectively.

The final classifier was exceptional for both the wake and NREM states. However, the poorest performance was noted for REM stage, which had a precision of 0.535 and the F1 of 0.664. Most of the misclassified stages were between NREM and REM. As REM state was the minority class (only 4% of the dataset), even a relatively small false positive rate would cause a high number of false positives which would overwhelm the rare true positives. For instance, 9.7% of REM bouts were incorrectly identified as NREM by the visual classifier, and 7.1% of the predicted REM bouts were actually NREM (FIG. 10C). These misclassification errors seem small, but could disproportionately affect the precision of the classifier due to the imbalance between REM and NREM. Despite this, the classifier was also able to correctly identify 89.7% of REM epochs present in the validation dataset.

Figure 11A:
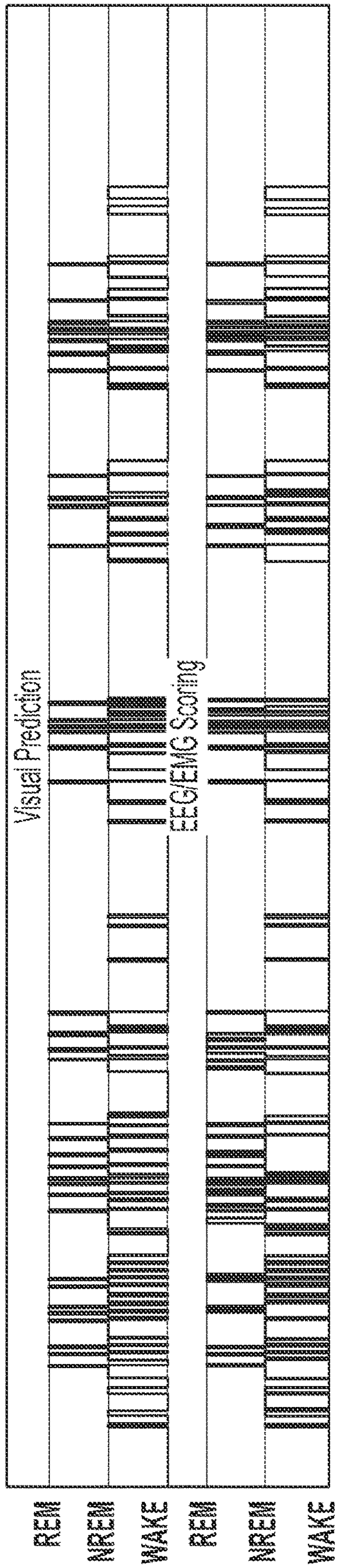
FIG. 11A-D presents graphs illustrating validation of visual scoring.
Figure 11B:
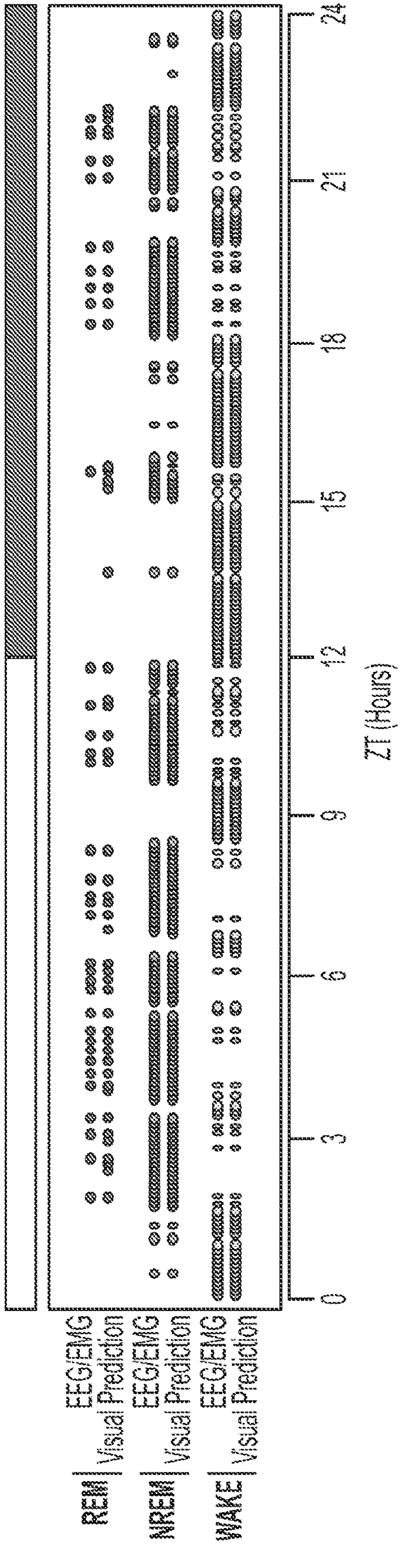
Figure 11C:
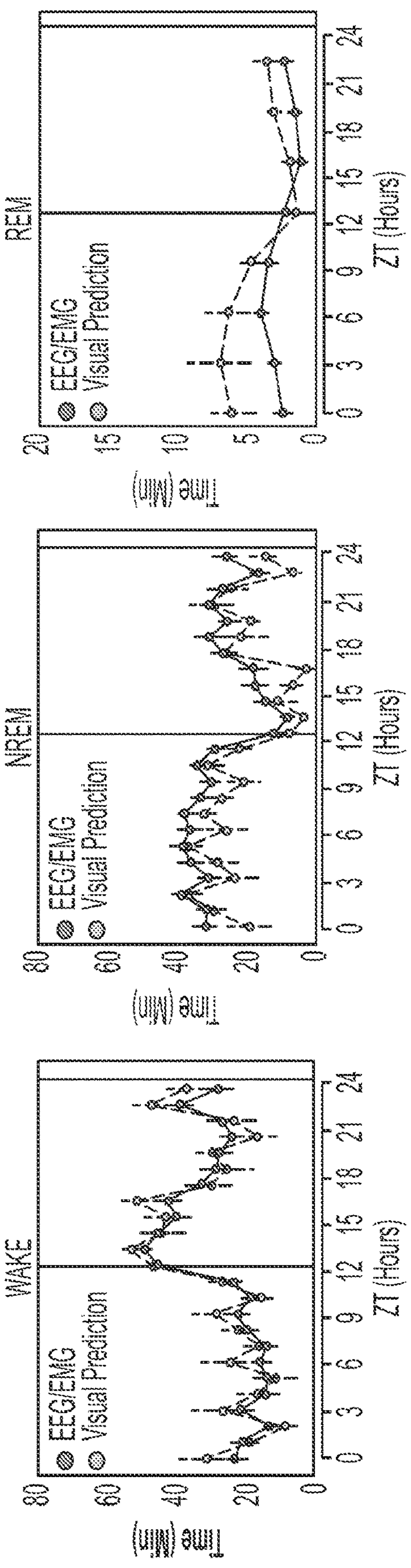
Figure 11D:
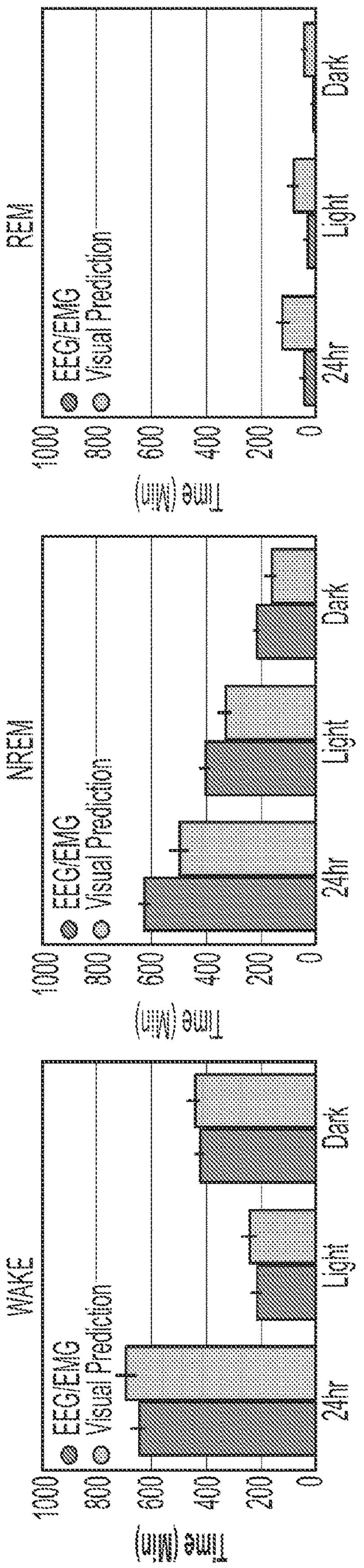

Within the context of other existing alternatives to EEG/EMG recordings, this model performed exceptionally. Table 5 compares respective performances of previously reported models to performance of the classifier model described herein. It is noted that each of the previously reported models used different datasets with different characteristics. Notably, the piezo system was evaluated on a balanced dataset which could have presented higher precision due to reduced possible false positives. The classifier approach developed herein outperformed all approaches for Wake and NREM state prediction. REM prediction was a more difficult task for all approaches. Of the machine learning approaches, the model described herein achieved the best accuracy. FIG. 11A and FIG. 11B display visual performance comparisons of our classifier to manually scoring by a human expert (hypnogram). The x axis is time, consisting of sequential epochs, and the y axis corresponds to the three stages. For each subfigure, the top panel represent the human scoring results and the bottom panel represent the scoring results of the classifier. The hypnogram shows accurate transitions between stages along with frequency of isolated false positives (FIG. 11A). We also plot visual and human scoring for a single animal over 24 hours (FIG. 11B). The raster plot shows more exceptional global correlation between state classification (FIG. 11B). We then compare all C57BL/6J animals between human EEG/EMG scoring and our visual scoring (FIG. 11C, D). We observe high correlation across all states and conclude that our visual classifier scoring results are consistent with human scores.

TABLE 5

Performance comparison across published approaches.

| | Wake | | | NREM | | | REM | | | |
|---|---|---|---|---|---|---|---|---|---|---|
| Approach | Acc. | Pr. | Re. | Acc. | Pr. | Re. | Acc. | Pr. | Re. | Overall |
| Video (mice) 34 | | | | | | | | | | 0.767 |
| Doppler (rats) 31 | 0.916 | 0.898 | 0.834 | 0.851 | 0.852 | 0.917 | 0.697 | 0.718 | 0.615 | 0.844 |
| Piezo (mice) 26 | 0.91 | 0.841 | 0.9 | 0.831 | 0.717 | 0.81 | 0.834 | 0.815 | 0.66 | 0.787 |
| Electric Field* (mice)33 | | | 0.938 | | 0.943 | 0.943 | | | 0.834 | 0.94 |
| Novel (mice) | 0.961 | 0.984 | 0.961 | 0.914 | 0.951 | 0.914 | 0.898 | 0.535 | 0.897 | 0.92 |

*Electric field approach uses human annotation, not a machine learning algorithm.

Figure 12:
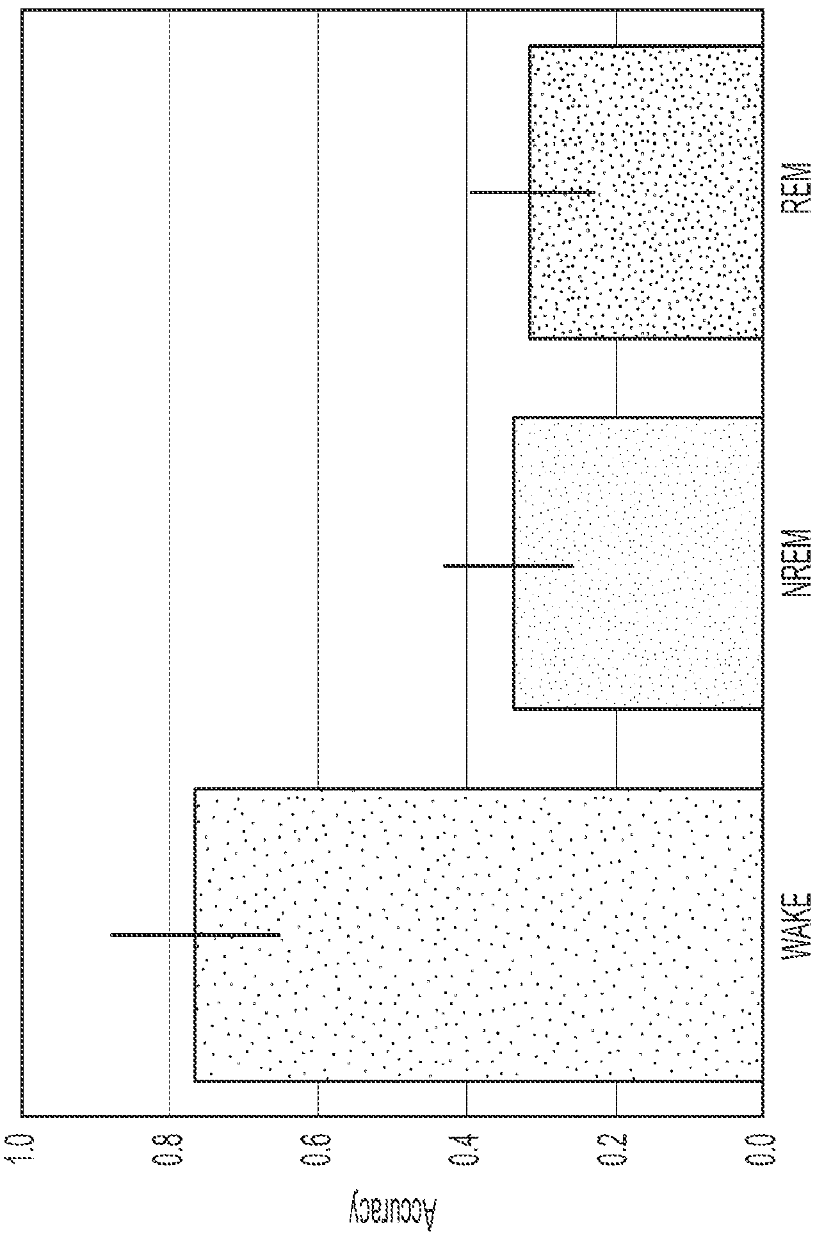
FIG. 12 presents a bar graph depicting results of additional data augmentation to the classifier model.

A variety of data augmentation approaches were also attempted to improve classifier performance. The proportion of the different sleep states in 24 hours was severely imbalanced (WAKE 48%, NREM 48%, and REM 4%). The typical augmentation techniques used for time series data include jittering, scaling, rotation, permutation, and cropping. These methods can be applied in combination with each other. It has previously been shown that the classification accuracy could be increased by augmenting the training set by combining four data augmentation techniques [Rashid, K. M. and Louis, *J. Adv Eng Inform.* 42:100944 (2019)]. However, it was decided to use a dynamic time warping based approach to augment the size of the training dataset for improving the classifier [Fawaz, H. I., et al., *arXiv:* 1808:02455] because the features extracted from the time series depended on the spectral composition. After data augmentation, the size of the dataset was increased about 25% (from 14K epochs to 17K epochs). It was observed that adding data through the augmentation algorithm decreased the prediction accuracy. The average prediction average for Wake, NREM, and REM states were 77%, 34%, and 31%. Although not desiring to be bound by any particular theory, the performance after data augmentation may have been due to introduction of more noise from the REM states data and decreased performance of the classifier. Performance was presented with 10-fold cross validation. The results of applying this data augmentation is shown in FIG. 12 and Table 6 (Table 6 shows numerical results of the data augmentation). This data augmentation approach did not improve classifier performance and was not pursued further. Overall, the visual sleep state classifier was able to accurately identify sleep states using only visual data. Inclusion of HMM, Hu moments, and highly accurate labels, improve performance, whereas data augmentation using dynamic time warping and motion amplification did not improve performance.

TABLE 6

Data augmentation results

| | Precision | Recall | F1 score |
|---|---|---|---|
| WAKE | 0.63 | 0.77 | 0.69 |
| NREM | 0.78 | 0.34 | 0.46 |
| REM | 0.68 | 0.31 | 0.11 |

DISCUSSION

Sleep disturbances are a hallmark of numerous diseases and high-throughput studies in model organisms are critical for discovery of new therapeutics [Webb, J. M. and Fu, Y-H., *Curr. Opin. Neurobiol.* 69: 19-24 (2021); Scammell, T. E. et al., *Neuron.* 93(4): 747-765 (2017); Allada, R, and Siegel, J. M. *Curr. Biol.* 18(15):R670-R679 (2008)]. Sleep studies in mice are challenging to conduct at scale due to the time investment for conducting surgery, recovery time, and scoring of recorded EEG/EMG signals. The system described herein provides a low-cost alternative to EEG/EMG scoring of mouse sleep behavior, enabling researchers to conduct larger scale sleep experiments that would previously have been cost prohibitive. Previous systems have been proposed to conduct such experiments but have only been shown to adequately distinguish between wake and sleep states. The system described herein builds on these approaches and can also distinguish the sleep state into REM and NREM states.

The system described herein achieves sensitive measurements of mouse movement and posture during sleep. This system has been shown to observe features that correlate with mouse breathing rates using only visual measurements. Previously published systems that can achieve this level of sensitivity include plethysmography [Bastianini, S. et al., *Sci. Rep.* 7:41698 (2017)] or piezo systems [Mang, G. M. et al., *Sleep.* 37(8): 1383-1392 (2014); Yaghouby, F., et al., *J.*

*Neurosci. Methods.* 259:90-100 (2016)]. Additionally, it has been shown herein that based on the features used, this novel system may be capable of identifying sub-clusters of NREM sleep epochs, which could shed additional light on the structure of mouse sleep.

In conclusion, high-throughput, non-invasive, computer vision-based methods described above herein for sleep state determination in mice are of utility to the community.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto: the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments or that one or more embodiments necessarily include logic for deciding, with or without other input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

All references, patents and patent applications and publications that are cited or referred to in this application are incorporated by reference in their entirety herein.

What is claimed is:

1. A computer-implemented method comprising:

receiving video data representing a video of a subject;

determining, using the video data, segmentation data indicating a first set of pixels corresponding to the subject and a second set of pixels corresponding to a background;

determining, based on the segmentation data, a plurality of visual features corresponding to the subject in each frame of the video data, wherein the visual features comprise a major axis length and a minor axis length;

determining time domain features for each of the plurality of visual features in the video data, wherein the time domain features are based on signals of the subject's visual features in the video data;

determining frequency domain features for each of the plurality of visual features in the video data, wherein the frequency domain features are based on signals of the subject's visual features in the video data; and processing, using a machine learning classifier, the time domain features and the frequency domain features to determine sleep state data.

2. The computer-implemented method of claim 1, further comprising:

processing, using a machine learning model, the video data to determine the segmentation data to identify the subject in the video data.

3. The computer-implemented method of claim 2, further comprising:

processing the segmentation data to determine ellipse data corresponding to the subject.

4. The computer-implemented method of claim 2, wherein determining the plurality of visual features comprises processing the segmentation data to determine the plurality of visual features.

5. The computer-implemented method of claim 1, further comprising:

determining time domain features for each visual feature of the plurality of visual features, wherein determining the time domain features comprises determining one of: kurtosis data, mean data, median data, standard deviation data, maximum data, and minimum data, and wherein the plurality of visual features comprises the time domain features.

6. The computer-implemented method of claim 1, further comprising:

determining frequency domain features for each visual feature of the plurality of visual features, wherein determining the frequency domain features comprises determining one of: kurtosis of power spectral density, skewness of power spectral density, mean power spectral density, total power spectral density, maximum data, minimum data, average data, and standard deviation of power spectral density, and wherein the plurality of visual features comprises the frequency domain features.

7. The computer-implemented method of claim 1, further comprising:

processing, using a machine learning classifier, the plurality of visual features to determine a sleep state for a video frame of the video data, the sleep state being one of a wake state, a REM sleep state and a non-REM (NREM) sleep state.

8. The computer-implemented method of claim 1, wherein the sleep state data indicates one or more of a duration of time of a sleep state, a duration and/or frequency interval of one or more of a wake state, a REM state, and a NREM state; and a change in one or more sleep states.

9. The computer-implemented method of claim 1, further comprising:

determining, using the plurality of visual features, a plurality of body areas of the subject, each body area of the plurality of body areas corresponding to a video frame of the video data; and determining the sleep state data based on changes in the plurality of body areas during the video.

10. The computer-implemented method of claim 1, further comprising:

determining, using the plurality of visual features, a plurality of width-length ratios, each width-length ratio of the plurality of width-length ratios corresponding to a video frame of the video data; and determining the sleep state data based on changes in the plurality of width-length ratios during the video.

11. The computer-implemented method of claim 1, wherein determining the sleep state data comprises:

detecting a transition from a NREM state to a REM state based on a change in a body area or body shape of the subject, the change in the body area or body shape being a result of muscle atonia.

12. The computer-implemented method of claim 1, further comprising:

determining a plurality of width-length ratios for the subject, a width-length ratio of the plurality of width-length ratios corresponding to a video frame of the video data;

determining time domain features using the plurality of width-length ratios;

determining frequency domain features using the plurality of width-length ratios, wherein the time domain features and the frequency domain features represent motion of an abdomen of the subject; and determining the sleep state data using the time domain features and the frequency domain features.

13. The computer-implemented method of claim 1, wherein the video captures the subject in the subject's natural state, wherein the subject's natural state comprises an absence of an invasive detection in or on the subject.

14. The computer-implemented method of claim 1, wherein the video is a high-resolution video.

15. The computer-implemented method of claim 1, further comprising:

processing, using a machine learning classifier, the plurality of visual features to determine a plurality of sleep state predictions each for one video frame of the video data; and processing, using a transition model, the plurality of sleep state predictions to determine a transition between a first sleep state to a second sleep state, wherein the transition model is a Hidden Markov Model.

16. The computer-implemented method of claim 1, wherein the video is of two or more subjects including at least a first subject and a second subject, and the method further comprises:

processing the video data to determine first segmentation data indicating a first set of pixels corresponding to the first subject;

processing the video data to determine second segmentation data indicating a second set of pixels corresponding to the second subject;

determining, using the first segmentation data, a first plurality of visual features corresponding to the first subject;

determining, using the first plurality of visual features, first sleep state data for the first subject;

determining, using the second segmentation data, a second plurality of visual features corresponding to the second subject; and determining, using the second plurality of visual features, second sleep data for the second subject.

17. The computer-implemented method of claim 1, wherein the subject is a rodent, and optionally is a mouse.

18. The computer-implemented method of claim 1, wherein the subject is a genetically engineered subject.

* * * * *